United States Patent [19]

Nakane et al.

[11] Patent Number: 4,654,355
[45] Date of Patent: Mar. 31, 1987

[54] 7-OXABICYCLOHEPTANE SUBSTITUTED AMIDE-THIOAMIDE PROSTAGLANDIN ANALOGS

[75] Inventors: Masami Nakane, Hopewell; Joyce Reid, Dayton, both of N.J.

[73] Assignee: E. R. Squibb & Sons, Inc., Princeton, N.J.

[21] Appl. No.: 761,261

[22] Filed: Aug. 1, 1985

[51] Int. Cl.[4] .................. C07D 443/08; C07D 405/14; A61K 31/34; A61K 31/41

[52] U.S. Cl. .................................... 514/382; 514/469; 548/252; 549/463

[58] Field of Search ........................ 548/252; 549/463; 514/469, 382

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,617 | 6/1984 | Nakane et al. | 514/469 |
| 4,525,479 | 6/1985 | Das et al. | 424/285 |
| 4,526,901 | 7/1985 | Nakane | 514/469 |

FOREIGN PATENT DOCUMENTS 0043292 8/1982 European Pat. Off. .
2039909 8/1980 United Kingdom .

*Primary Examiner*—Robert Gerstl
*Attorney, Agent, or Firm*—Lawrence S. Levinson; Burton Rodney

[57] ABSTRACT

7-Oxabicycloheptane substituted amide-thioamide prostaglandin analogs are provided having the structural formula

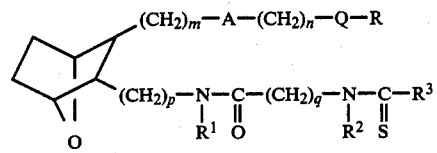

wherein m is 0 to 4; A is —CH=CH— or —CH$_2$CH$_2$—; n is 1 to 5; Q is —CH=CH—, —CH$_2$—,

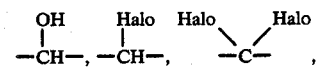

or a single bond; R is CO$_2$H, CO$_2$alkyl, CO$_2$alkali metal, CO$_2$polyhydroxyamine salt, —CH$_2$OH,

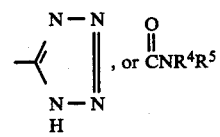

wherein R$^4$ and R$^5$ are the same or different and are H, lower alkyl, hydroxy, lower alkoxy or aryl, at least one of R$^4$ and R$^5$ being other than hydroxy and lower alkoxy; p is 1 to 4; R$^1$ is H or lower alkyl; q is 1 to 12; R$^2$ is H or lower alkyl; and R$^3$ is H, lower alkyl, lower alkenyl, lower alkynyl, aryl, arylalkyl, lower alkoxy, aralkyloxy, amino, alkylamino, or arylamino.

The compounds are cardiovascular agents useful, for example, in the treatment of thrombotic disease.

16 Claims, No Drawings

7-OXABICYCLOHEPTANE SUBSTITUTED AMIDE-THIOAMIDE PROSTAGLANDIN ANALOGS

DESCRIPTION OF THE INVENTION

The present invention relates to 7-oxabicycloheptane substituted amide-thioamide prostaglandin analogs which are cardiovascular agents useful, for example, in the treatment of thrombotic disease. These compounds have the structural formula

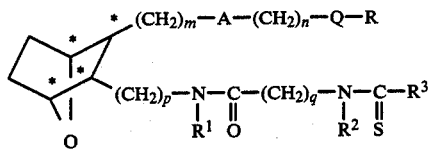

including all stereoisomers thereof, wherein m is 0 to 4; A is —CH=CH— or —CH$_2$—CH$_2$—; n is 1 to 5; Q is —CH=CH—, —CH$_2$—,

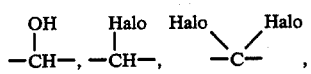

or a single bond; R is CO$_2$H, CO$_2$alkyl, CO$_2$ alkali metal, CO$_2$polyhydroxyamine salt, —CH$_2$OH,

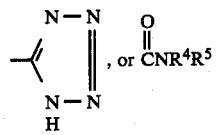

wherein R$^4$ and R$^5$ are the same or different and are H, lower alkyl, hydroxy, lower alkoxy or aryl at least one of R$^4$ and R$^5$ being other than hydroxy and lower alkoxy; p is 1 to 4; R$^1$ is H or lower alkyl; q is 1 to 12; R$^2$ is H or lower alkyl; and R$^3$ is H, lower alkyl, lower alkenyl, lower alkynyl, aryl, arylalkyl, lower alkoxy, aralkyloxy, amino, alkylamino, or arylamino.

The term "lower alkyl" or "alkyl" as employed herein alone or as part of another group includes both straight and branched chain hydrocarbon radicals of from 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups, 1 or 2 amino groups, 1 or 2 nitrogroups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitrogroups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbonsin the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms (CH$_2$)$_m$, (CH$_2$)$_n$ and (CH$_2$)$_p$ includes straight or branched chain radicals having from 0 to 4 carbons in the normal chain in the case of (CH$_2$)$_m$, from 1 to 5 carbons in the normal chain in the case of (CH$_2$)$_n$ and from 1 to 4 carbons in the normal chain in the case of (CH$_2$)$_p$ and may contain one or more lower alkyl and/or halogen substituents. Examples of (CH$_2$)$_m$, (CH$_2$)$_n$ and (CH$_2$)$_p$ groups include

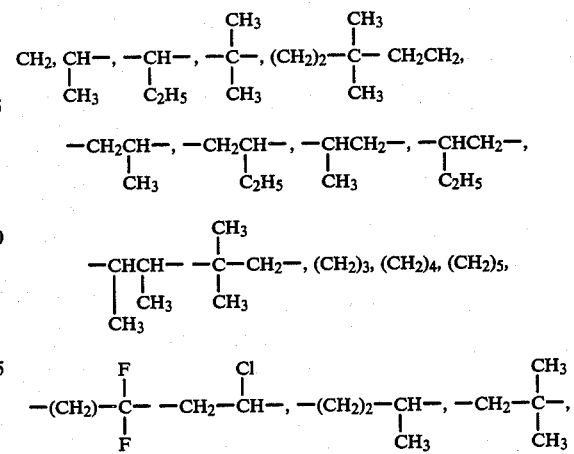

-continued

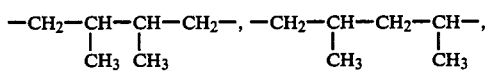

and the like.

The term $(CH_2)_q$ includes straight or branched chain radicals having from 1 to 12 carbons in the normal chain and includes any of the above examples of $(CH_2)_m$, $(CH_2)_n$ and $(CH_2)_p$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

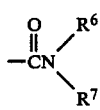

wherein $R^6$ and $R^7$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I. wherein m is 1 or 2, A is a —CH=CH—, n is 1 or 4, Q is a single bond or —C(F$_2$)—,

$(CH_2)_2$, or —CH=CH, R is $CO_2H$ or $CH_2OH$; p is 1, $R^1$ is H, $(CH_2)_q$ is —CH$_2$—; $R^2$ is H or $CH_3$, and $R^3$ is lower alkyl, such as pentyl, hexyl, or heptyl or lower alkoxy, such as pentoxy, or lower alkylamino such as pentylamino.

The compounds of formula I of the invention may be prepared as described below.

A. p is 1, m is 1, Q is —CH$_2$— or a single bond and $R^1$ is H

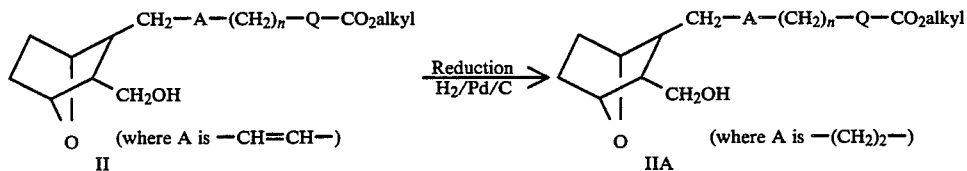

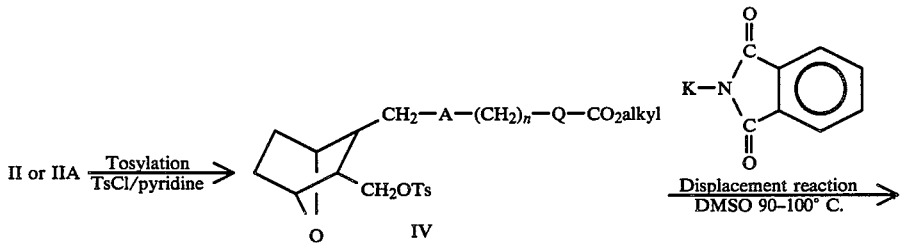

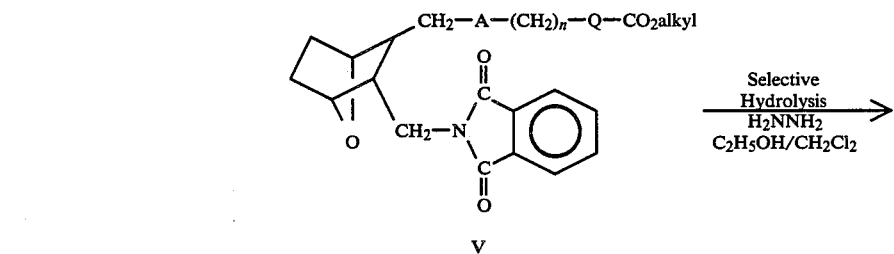

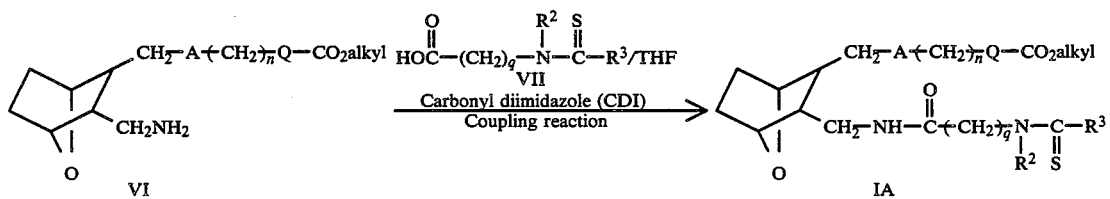

A'. Where p is 1, m is 1, Q is —CH$_2$— or a single bond and $R^1$ is alkyl

-continued
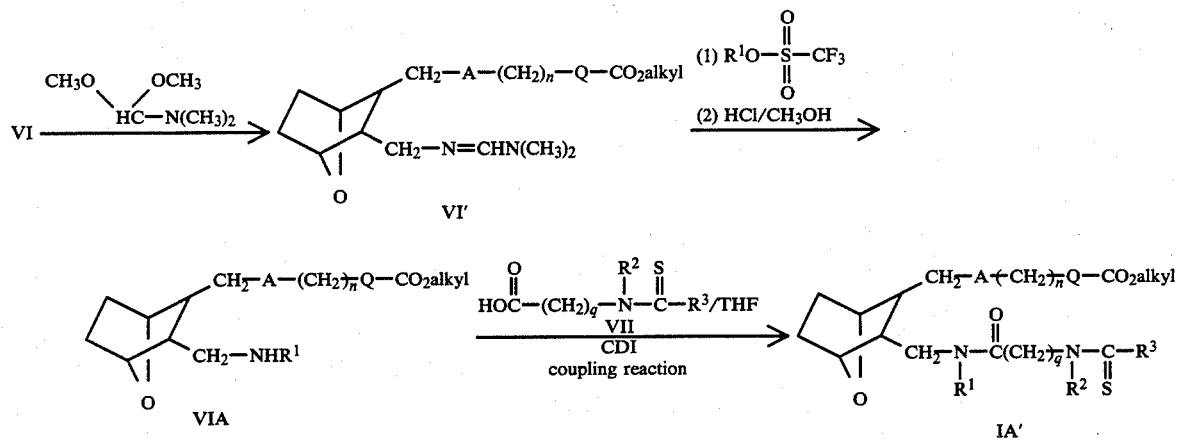
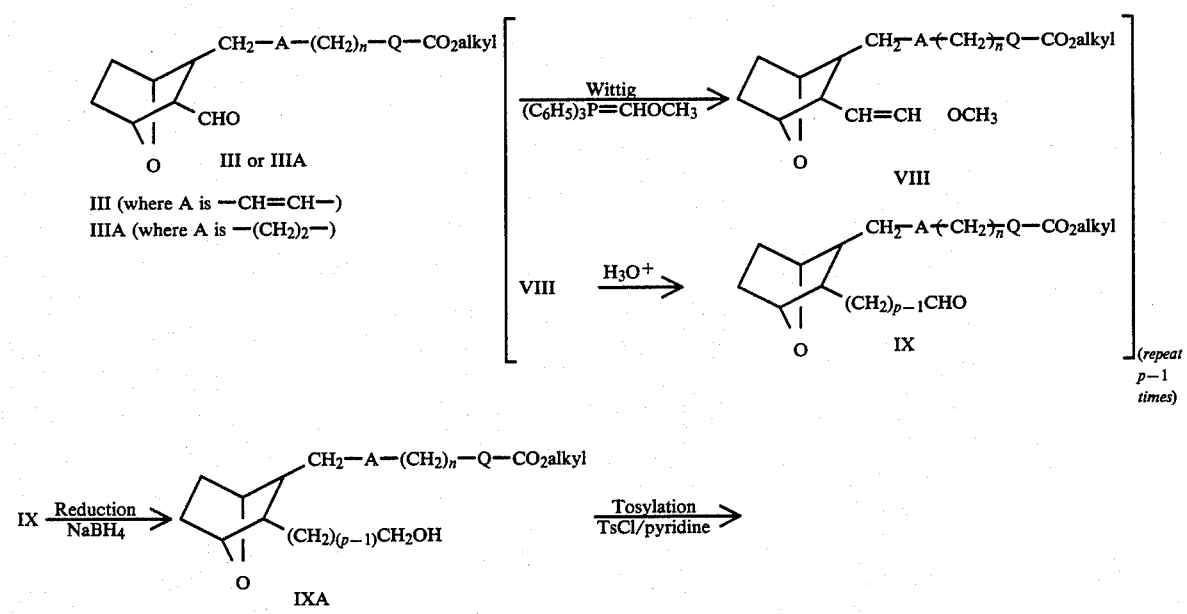
B. Where Q is $CH_2$ or a single bond, p is 2 to 5, m is 1 and $R^1$ is H
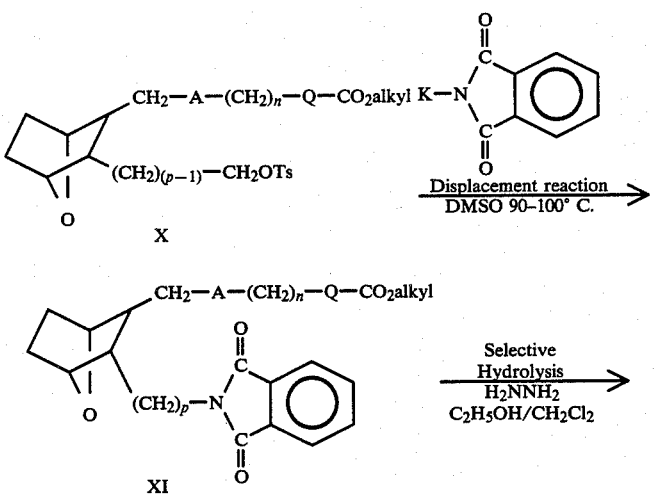

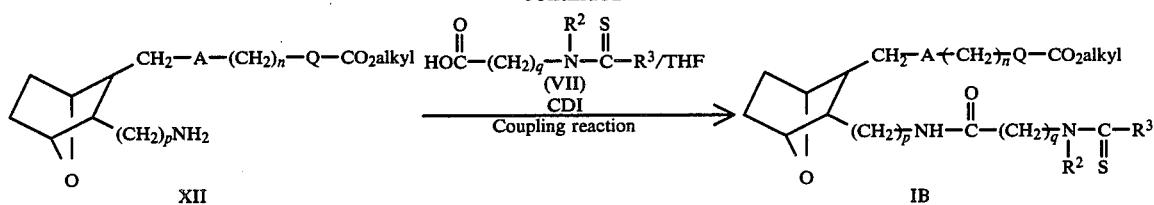
B'. Where Q is CH₂ or a single bond, p is 2 to 5, m is 1 and $R^1$ is alkyl
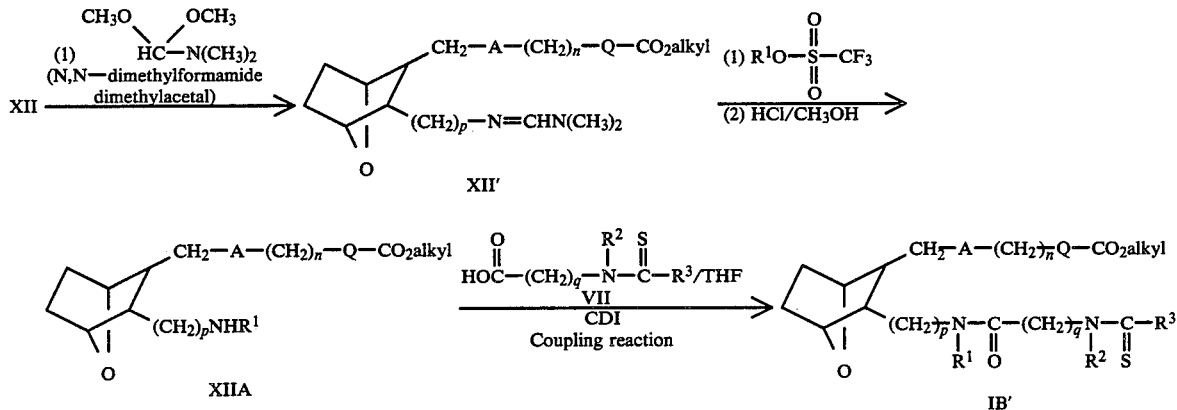
C. Where m is 2, p is 1, A is —CH=CH— and Q is CH₂ or a single bond
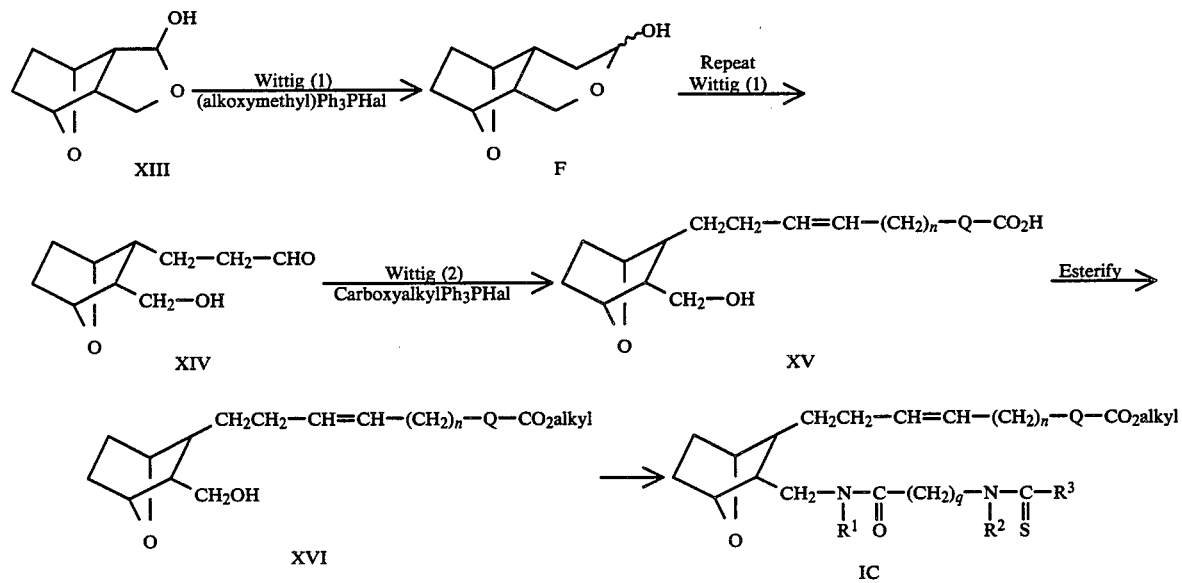
D. m is 2, p is 1, A is —CH₂—CH₂— and Q is CH₂ or a single bond
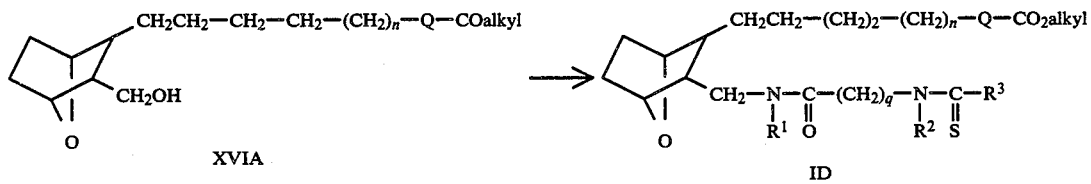
E. Where m is 3 or 4, p is 1, A is —CH=CH— and Q is CH₂ or a single bond

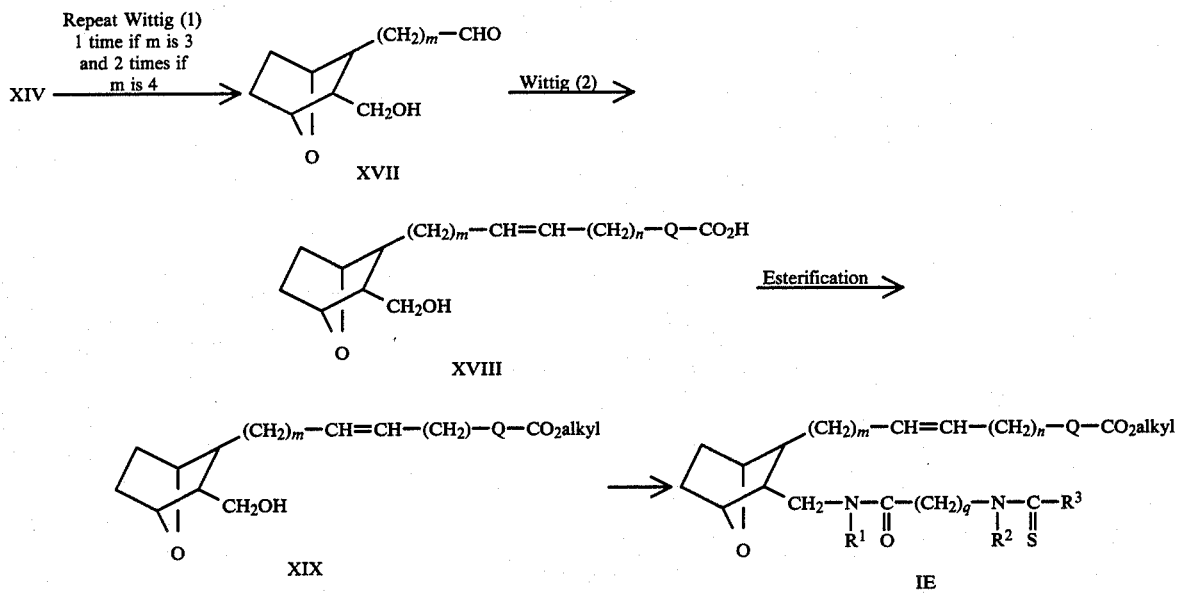
F. Where m is 3 or 4, p is 1, A is CH₂CH₂ and Q is CH₂ or a single bond
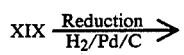
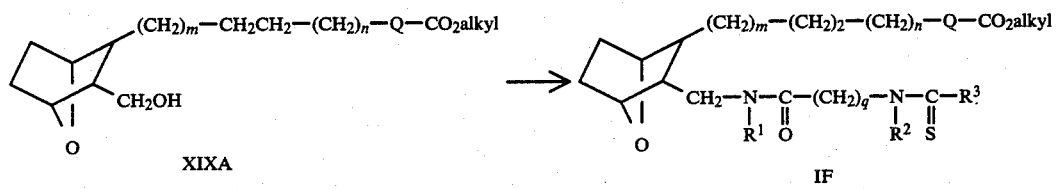
G. Where m = 0, A is —CH=CH—, p is 1, Q is CH₂ or a single bond
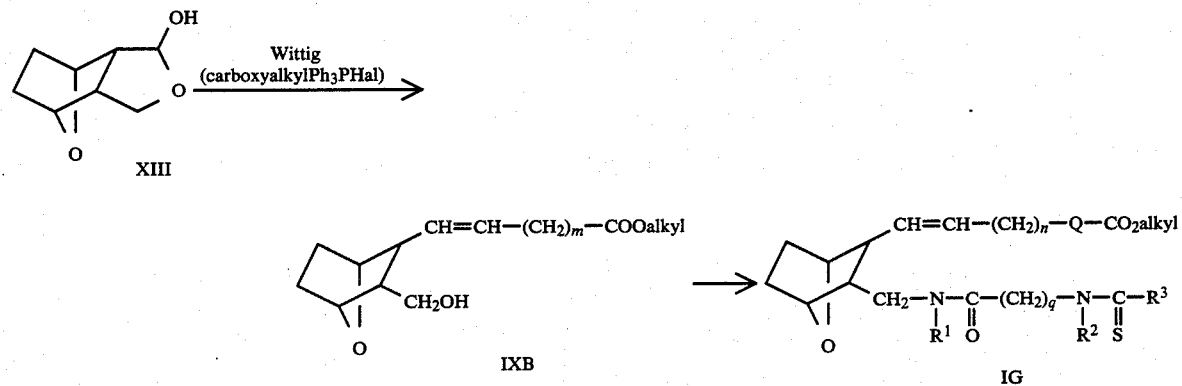
H. Where m = 0, A is —(CH₂)₂—, p is 1, Q is CH₂ or a single bond
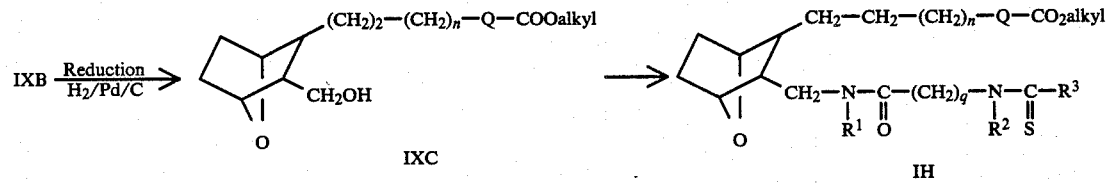
I. Where Q is —CH=CH—

-continued
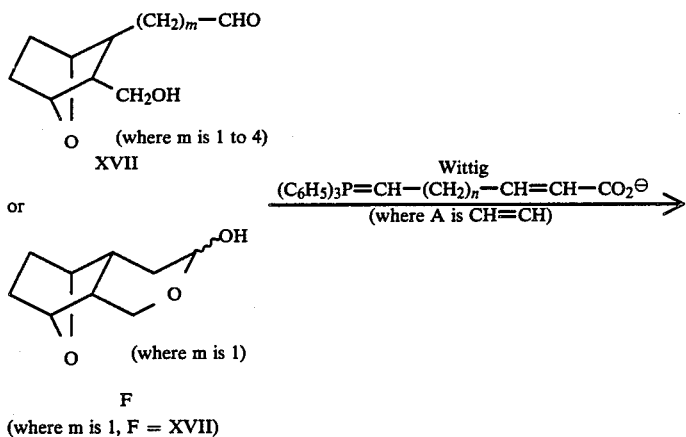
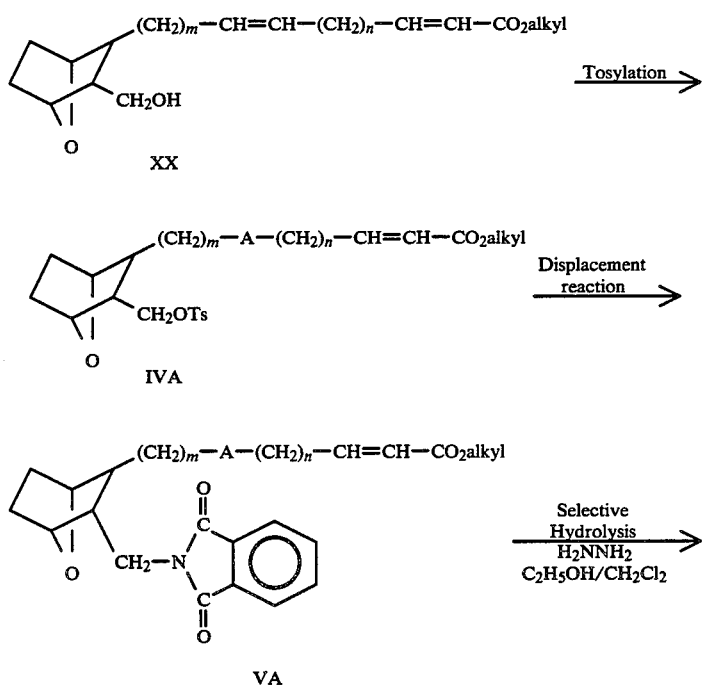
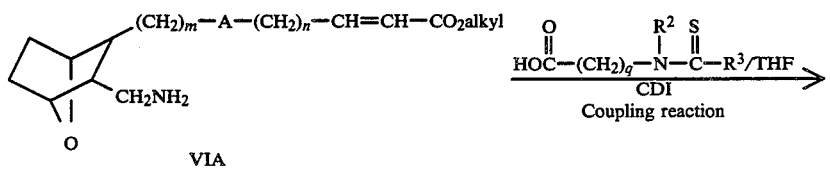
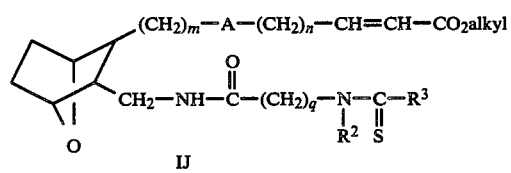
J. Where Q is —CH— or —C—
          |       \|/
         halo   halo halo halo

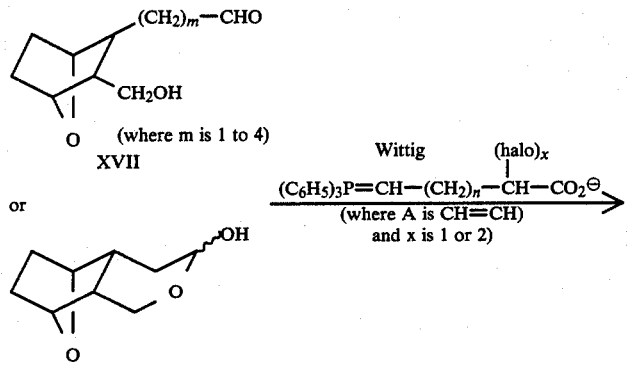
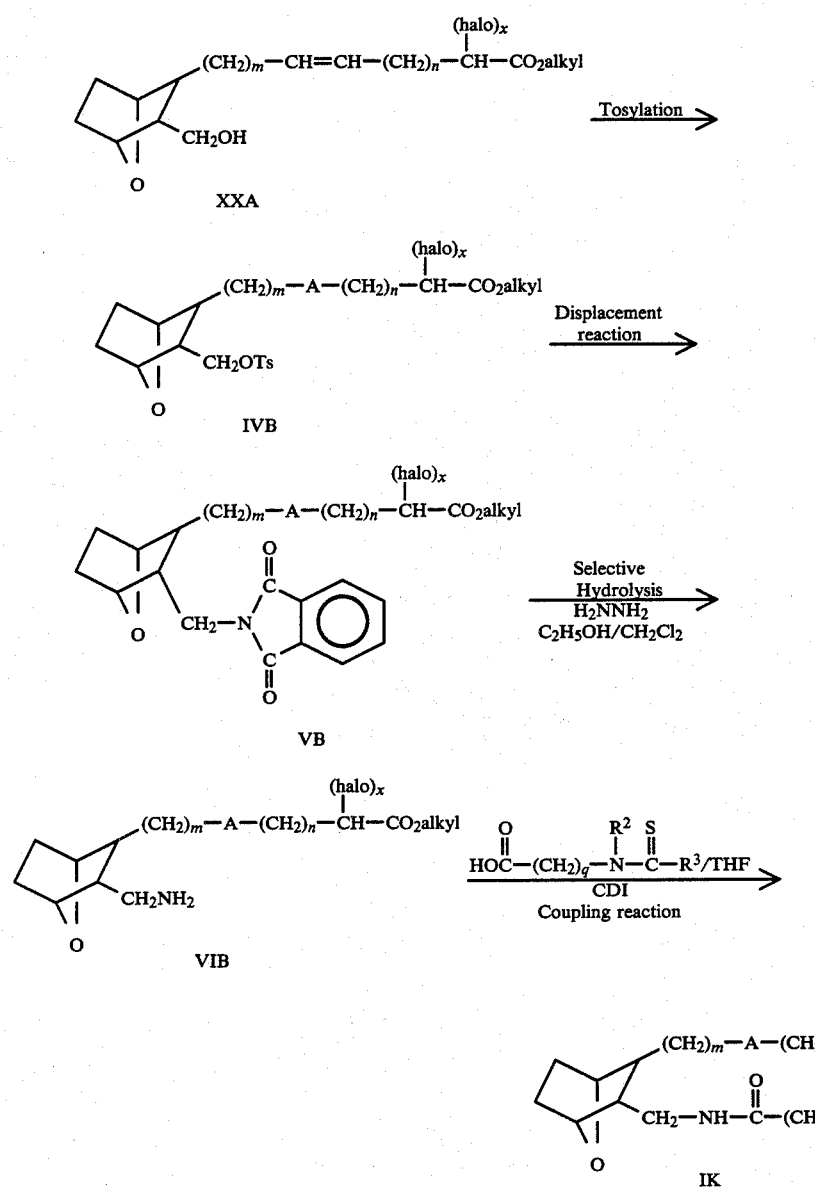
K. Where Q is $-\overset{OH}{\underset{|}{CH}}-$

-continued
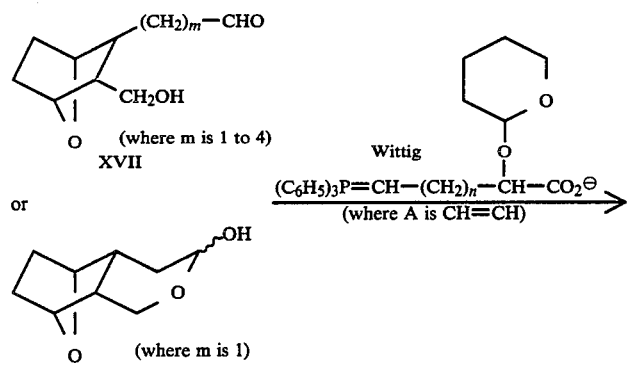
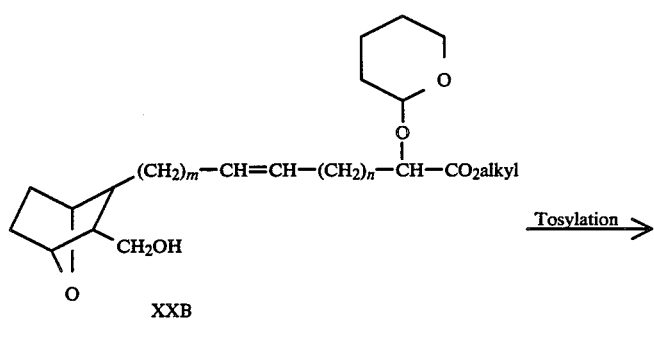
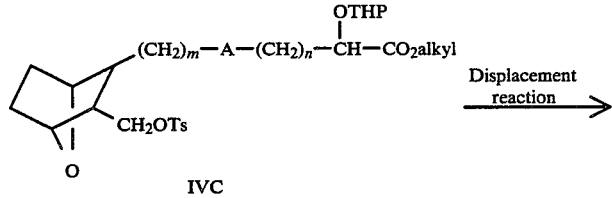
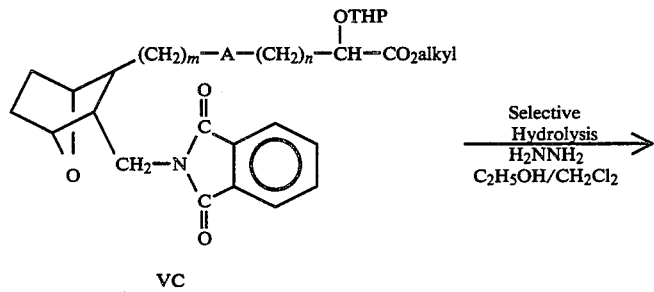
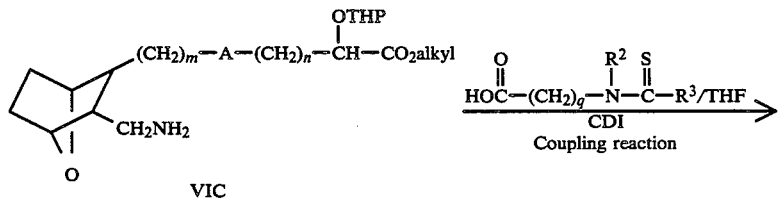

-continued
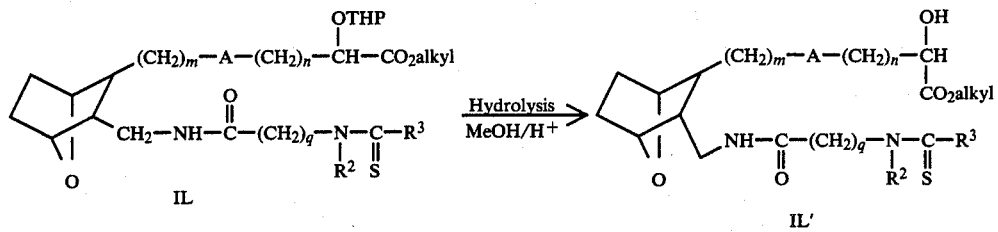
L. Where R is $\overset{O}{\overset{\|}{C}}NR^4R^5$ (wherein $R^4$ and $R^5$ are other than hydroxy or alkoxy)
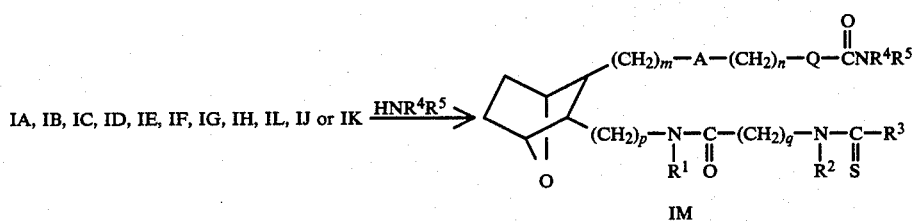
M. Where R is 
and A is CH=CH
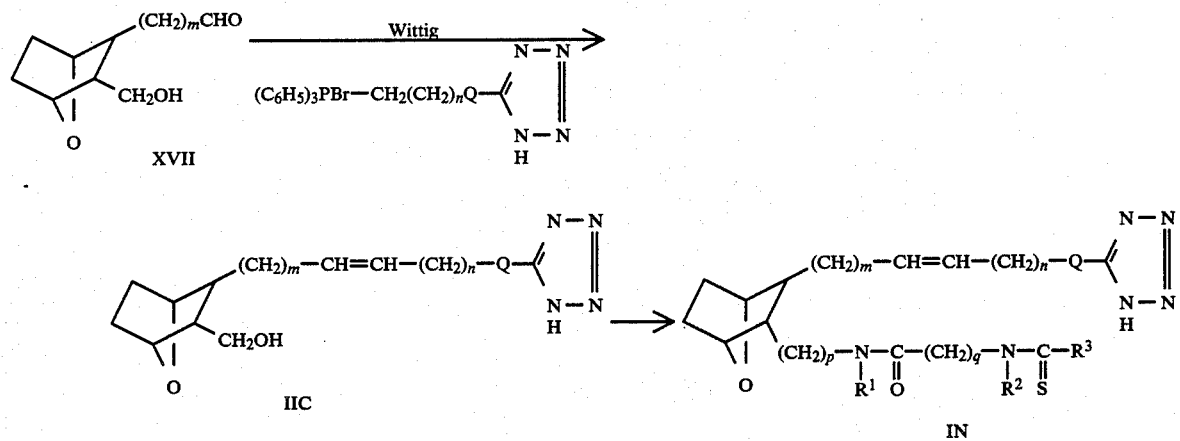
N. Where R is 
and A is $(CH_2)_2$
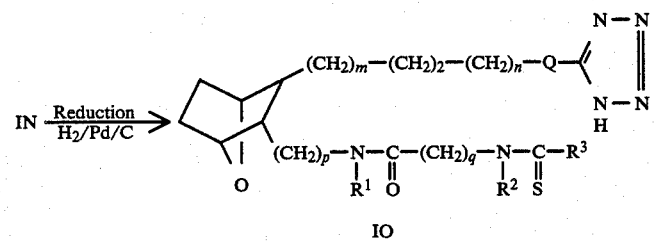
O. Where R is $CH_2OH$ -continued IA to IH, IL, or esters of IJ and IK $\xrightarrow{\text{NaBH}_4 \text{ or LiBH}_4}$

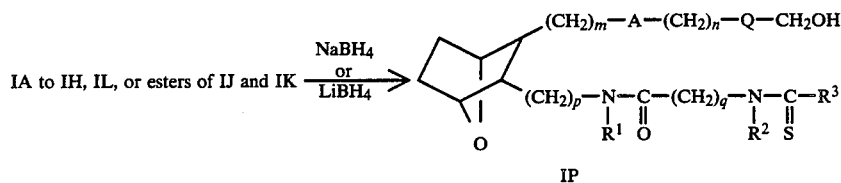

IP

P. Where R is CO$_2$H

IA to IH, IL $\xrightarrow{\text{Hydrolysis} \atop \text{LiOH, HCl}}$

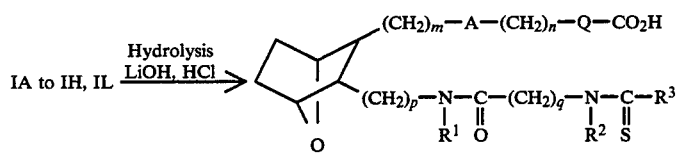

(IQ where A is CH=CH)
(IR where A is (CH$_2$)$_2$)

Q. Where R is $\overset{\text{O}}{\underset{\underset{R^4}{|}}{\overset{\|}{C}}}$N—OR$^{5'}$

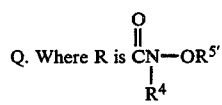

IQ or IR $\xrightarrow[\text{(2) HN}\diagdown_{R^4}^{OR^{5'}} \cdot \text{HCl/(C}_2\text{H}_5)_3\text{N}]{\text{Hydroxamate Formation (1) carbonyl-diimidazole (CDI)}}$ (wherein R$^{5'}$ is H or alkyl)

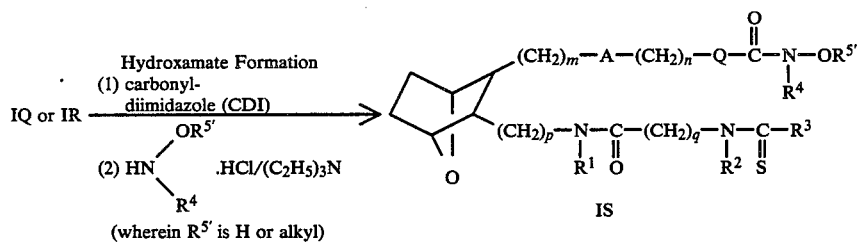

IS

R. Where R$^3$ is NH$_2$

VI, VIA or XII + HO$_2$C—CH$_2$—NH—$\overset{\text{S}}{\overset{\|}{C}}$—NH$_2$ $\xrightarrow{\text{(1) carbonyldiimidazole} \atop \text{(2) hydrolysis}}$

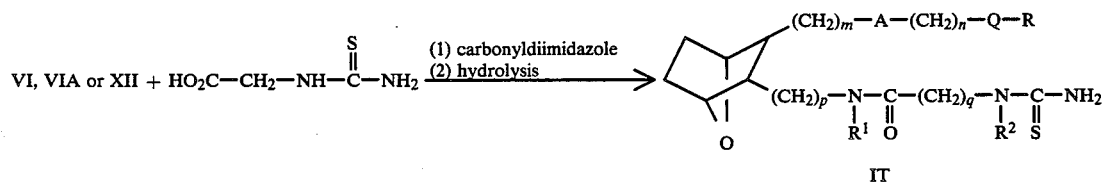

IT

As seen in reaction sequence "A", compounds of the invention where m is 1, —CH$_2$— or a single bond, p is 1, R is CO$_2$ alkyl, and R$^1$ is H, that is

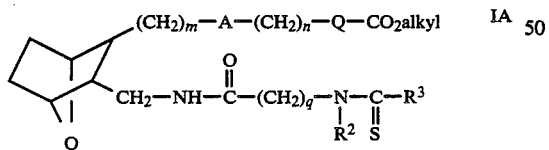

IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

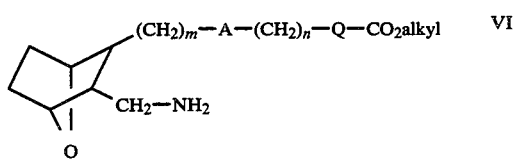

VI

As seen in reaction sequence "A'", where R$^1$ is lower alkyl, an alkylation reaction is carried out as in the reference M. J. O'Donnell et al., Tetrahedron Lett. (1984), 25, 3651-3654 to give VIA

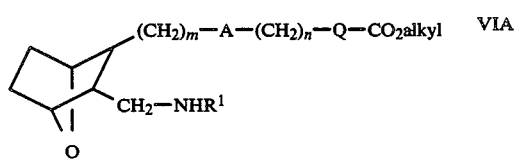

VIA

The amine VI or VIA is then subjected to a CDI coupling reaction by reacting VI or VIA with acid VII

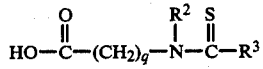

in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound of the invention IA or IA′

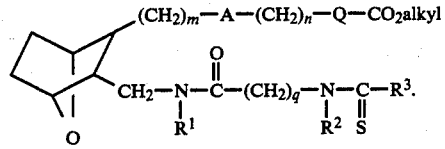

(IA - where $R^1$ is H IA′ - where $R^1$ is lower alkyl)

The reaction sequences identified as "B" and "B′" are employed to prepare compounds of the invention wherein Q is —$CH_2$— or a single bond, p is 2 to 5, and R is $CO_2$alkyl, that is,

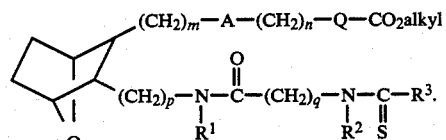

(where p is 2 to 5)
(IB - where $R^1$ is H IB′ - where $R^1$ is alkyl)

Compound II or IIA is used to form the aldehyde III (where A is —CH=CH—) or IIIA (where A is —($CH_2)_2$). Thus, to form aldehyde III where A is —CH=CH—, compound II is subjected to a Collins oxidation, for example, by reacting II with chromium trioxide in pyridine. To form the aldehyde IIIA (where A is ($CH_2)_2$) compound II is reduced, for example, with hydrogen over a palladium on carbon catalyst, to form hydroxymethyl compound IIA (where A is ($CH_2)_2$) and compound IIA is subjected to a Collins oxidation to form aldehyde IIIA (where A is ($CH_2)_2$). The aldehyde III or IIIA is used to prepare aldehyde IX (where p is 2-5) by carrying out a homologation sequence, such as Wittig reaction with $(C_6H_5)_3P$=CHOMe followed by hydrolysis, (p-1) times. The aldehyde IX (where p is 2-5) is then carried on to compounds of this invention where p is 2-5, that is

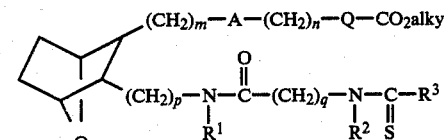

(where p is 2 to 5)

by reducing aldehyde IX by reacting with a reducing agent such as sodium borohydride to form alcohol IXA

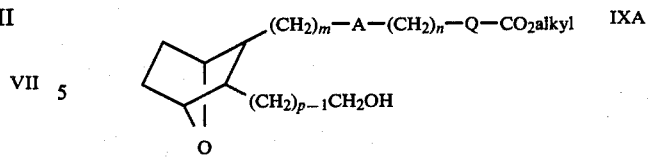

tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

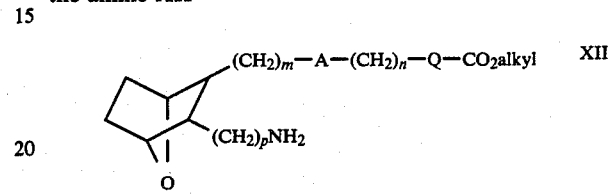

As seen in reaction sequence "B′", where $R^1$ is lower alkyl, an alkylation reaction is carried out as in O'Donnell et al, supra to give XIIA

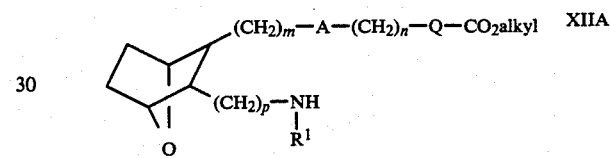

The amine XII or XIIA is then reacted with acid VII in a CDI coupling reaction as described above to form the amide ester compound of the invention IB or IB′

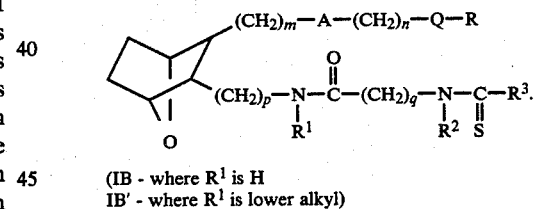

(IB - where $R^1$ is H
IB′ - where $R^1$ is lower alkyl)

Compounds of the invention wherein m is 2, A is —CH=CH—, p is 1 and Q is $CH_2$ or a single bond may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride; for example, as described in Example 4 of U.S. Pat. No. 4,143,054, to form compound F. The Wittig (1) procedure is repeated on compound F to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —$CH_2$—$CH_2$—, p is 1 and Q is CH$_2$ or a single bond may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH=CH—, p is 1 and Q is CH$_2$ or a single bond may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is CH$_2$CH$_2$, p is 1 and Q is CH$_2$ or a single bond may be prepared by reducing hydroxymethyl compound XIX to form compound XIXA which is then employed in place of compound II in reaction scheme "A" to form compound IF of the invention.

Thus, compounds of the invention wherein m is 0, 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

Referring now to reaction sequence "G", compounds of the invention wherein m is 0, A is CH=CH, p is 1 and Q is CH$_2$ or a single bond, that is, compound IG may be prepared by subjecting compound XIII (prepared as described in Example 3 of U.S. Pat. No. 4,143,054) to a Wittig reaction, for example, as described in Example 6(c) of U.S. Pat. No. 4,143,054, by reacting B with a carboxyalkyltriphenyl phosphonium halide, such as carboxypentyltriphenyl phosphonium bromide to form the hydroxymethyl compound IXB which may then be used to form the ester IG which, in turn, may be hydrolyzed to the corresponding acid.

As seen in reaction sequence "H", where it is desired to prepare compounds of the invention wherein m is 0 and A is (CH$_2$)$_2$, the hydroxymethyl compound IXB is reduced by treatment with hydrogen in the presence of a palladium on carbon catalyst to form hydroxymethyl compound IXC which may then be used to form ester IH which then may be hydrolyzed to the corresponding acid.

Referring to reaction sequence "I", compounds of formula I of the invention wherein Q is —CH=CH—, that is IJ

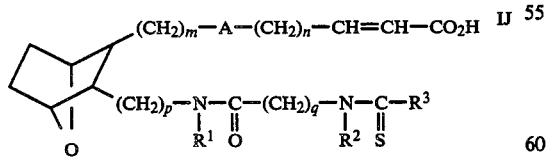

may be prepared by subjecting aldehyde XVII or compound F (where m is 1) to a Wittig reaction by reacting same with Wittig reagent C

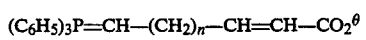

to form alcohol XX

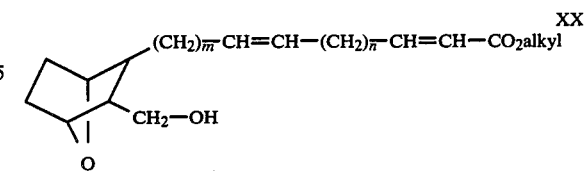

which is then employed in place of alcohol II or IIA in reaction sequence "A" to form IJ.

In reaction sequence "J" compounds wherein Q is

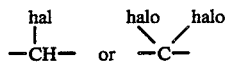

are prepared by sujecting XVII or F (where m is 1) to a Wittig reaction with

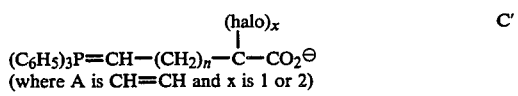

to form alcohol XXA

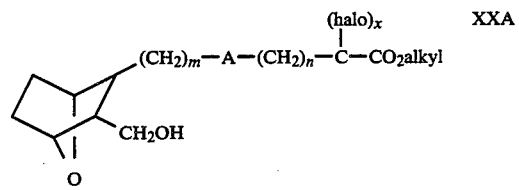

which is then employed in place of alcohol II or IIA in reaction sequence "A" to form IK.

As seen in reaction sequence "K" compounds of the invention wherein Q is

that is, IL, are formed by reacting XVII or F (where m is 1) with Wittig reagent C''

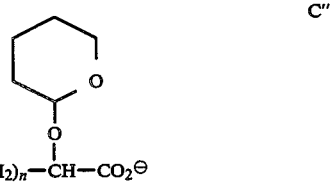

(prepared from the corresponding hydroxy compound employing conventional procedures) to form alcohol XXB

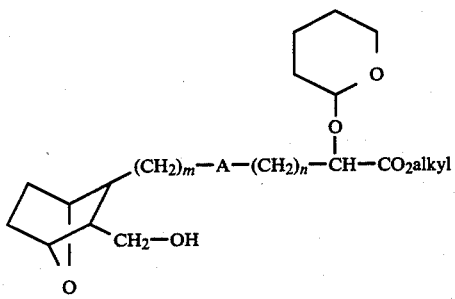                                                                XXB which is then employed in place of alcohol II or IIA in reaction sequence "A" to form IL which is hydrolyzed to IL'.

In reaction sequence "L", amides of the invention of structure IM

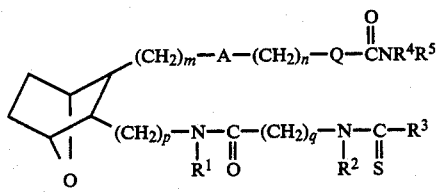                                                                IM wherein $R^4$ and $R^5$ are independently H, alkyl or aryl are prepared by trating ester IA to IH or IL or esters of IJ or IK with an amine of the structure

                                                                E

Compounds of the invention wherein R is tetrazole

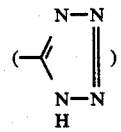

and A is CH=CH are prepared as described in reaction sequence "M" wherein alcohol XVII

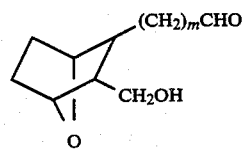                                                                XVII (prepared as described in U.S. Pat. No. 4,143,054) is reacted with a Wittig reagent of the structure G

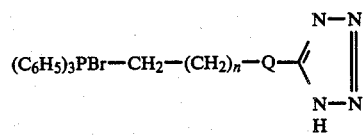                                                                G in the presence of a base, such as potassium t-butoxide or sodium hydride-dimethyl sulfoxide employing a molar ratio of F:G of within the range of from about 1:1 to about 0.2:1 to form the hydroxymethyl compound IIC

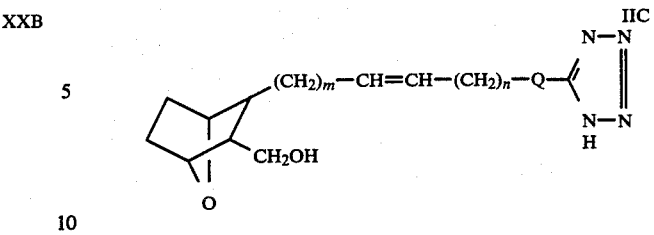                                                                IIC which may then be employed in reaction sequences "A" and "B" in place of compounds II or IIA to form compounds of the invention IN where A is —CH=CH— or IO where A is $(CH_2)_2$

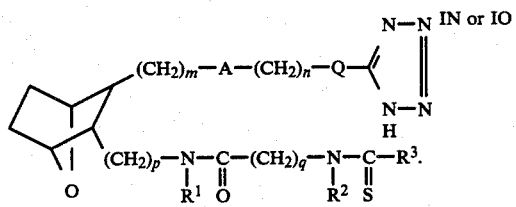                                                                IN or IO Alternatively, compound IO may be prepared by reducing compound IN by treating with $H_2$ in the presence of palladium on charcoal.

As seen in reaction sequence "O", compounds of the invention wherein R is $CH_2OH$ may be prepared by reducing esters IA to IH, and IL and esters of J and K by treatment with sodium borohydride or lithium borohydride to form compounds of the invention IP

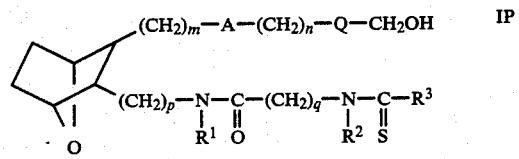                                                                IP

Referring to reaction sequence "P", the esters IA, IA', IB, IB' to IH and IL can be converted to the free acid, that is, to

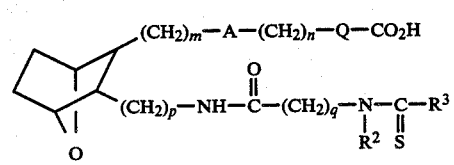

IQ (A is —CH=CH—)
IR (A is $(CH_2)_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IO and IR.

In the reaction sequence identified as "Q" where in Formula I, R is

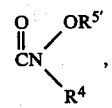

wherein $R^{5'}$ is H or alkyl, a solution of acid dissolved in an inert organic solvent such as tetrahydrofuran (THF) is treated with carbonyl diimidazole and the mixture is stirred at room temperature under nitrogen. The resulting active ester is added dropwise into a cold solution of amine hydrochloride H

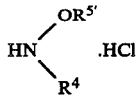

(wherein $R^{5'}$ is H or alkyl, employing a molar ratio of acid chloride:H of within the range of from about 0.3:1 to about 1:1 and preferably from about 0.5:1) and triethylamine in tetrahydrofuran to form the hydroxamate IS.

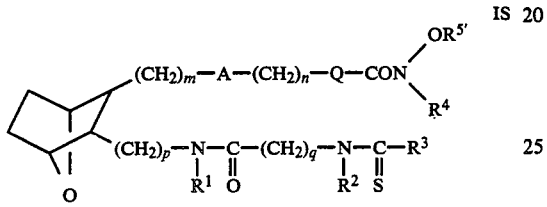

In reaction sequence "R" compounds of the invention wherein $R^3$ is $NH_2$, that is IT

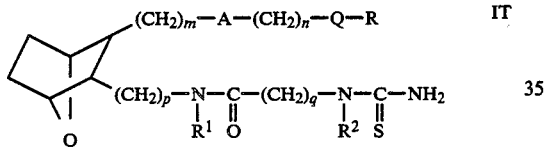

may be prepared by reacting amine VI, VIA or XII with N-(aminothioxo)glycine in the presence of carbonyldiimidazole and then hydrolyzing the resulting product to form IT.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The starting acid VII

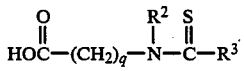

may be prepared by reacting the amino acid ester J

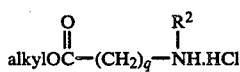

with acid chloride K

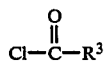

in the presence of a base such as sodium carbonate and ether and water to form L

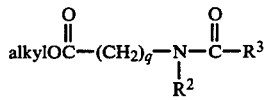

and reacting L with phosphorus pentasulfide or Lawesson's reagent to form M

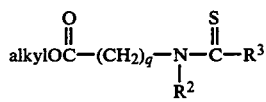

which is treated with strong base and water to form acid VII.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

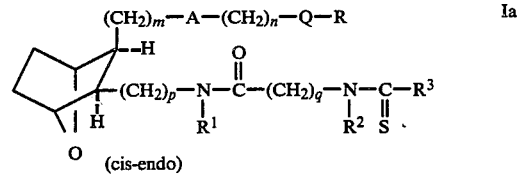

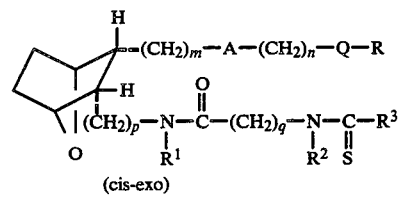

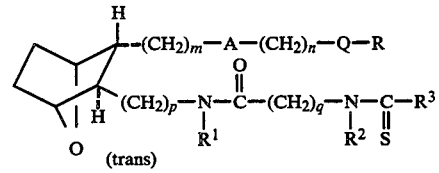

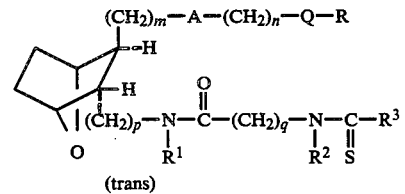

The nucleus in each of the compounds of the invention is depicted as

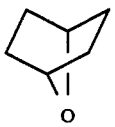

for matter of convenience; it will also be appreciated that the nucleus in the compounds of the invention may be depicted as

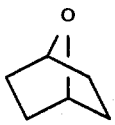

The compounds of this invetnion are cardiovascular agents useful as platelet aggregation inhibitors, such as in inhibiting arachidonic acid-induced platelet aggregation, e.g., for treatment of thrombotic disease such as coronary or cerebral thromboses, and in inhibiting broncho-constriction. They are also selective thromboxane A₂ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1β,2α(5Z),3α,4β]]-7-[3-[[[[(1-Thioxohexyl-)amino]acetyl]amino]methyl]-7-oxabicyclo[2.2.1]hept-2-yl]-5-heptenoic acid, methyl ester

A. [(1-Thioxohexyl)amino]acetic acid (1) Ethyl [(1oxohexyl)amine]acetate

Glycine ethyl ester hydrochloride (9.52 g, 70 mmol) was added to a cooled mixture of Na₂CO₃ (7.63 g, 72 mmol) in water (70 ml) and ether (70 ml). A solution of hexanoyl chloride (9.82 ml) in ether (10 ml) was added by fast dropwise addition. The ice bath was removed and the mixture was stirred at room temperature 1 hour. Saturated NaHCO₃ solution (50 ml) was added and the layers were separated. The aqueous layer was reextracted with ether (50 ml). The combined ether layers were washed with saturated NaHCO₃ solution (50 ml), 1N HCl solution (50 ml) and water (3×50 ml), dried (MgSO₄) and freed of solvent in vacuo leaving title intermediate as a straw colored oil (11.24 g, 80%).

(2) Ethyl [(1-thioxohexyl)amino]acetate

Phosphorus (IV) sulfide (5.64 mmol) was suspended in freshly distilled benzene (10 ml) in an argon atmosphere. A solution of the amide (3.78 g, 18.8 mmol, prepared as described in Part (1)) in distilled benzene (5 ml) was added and the mixture was heated at 75°–80° C. for 1 hour and 20 minutes. After cooling to room temperature, ice (about 10 g) was added and the mixture was stirred 10 minutes, then saturated NaHCO₃ solution (15 ml) was added and stirring was continued 10 minutes. Ether (50 ml) was added and the layers were separated. The aqueous layer was reextracted with ether (30 ml). The combined ether layers were washed with NaHCO₃ solution (10 ml) and water (20 ml), dried (MgSO₄), filtered and freed of solvent in vacuo leaving an oil (4.23 g). This was chromatographed on silica gel (145 g, Baker for flash chromatography), eluting with ether-hexane 1:2 to give title (2) intermediate as an oil (1.19 g, 29%). TLC: silica gel ether-hexane 1:1, UV+-PMA, $R_f$=0.39.

(3) [(1-Thioxohexyl)amino]acetic acid

The Part (2) ethyl ester (1.19 g, 5.48 mmol) was treated with a solution of NaOH (3 g, 75 mmol) in water (45 ml). After stirring at room temperature 45 minutes, the mixture was washed with ether (2×50 ml). The aqueous solution was acidified with concentrated HCl and the product was extracted into ether (2×50 ml). The extracts were dried (MgSO₄) and freed of solvent in vacuo leaving material which was crystalline. This was recrystallized from benzene to give title (3) acid (596 mg, 58%), m.p. 106°–109° C.

B. [1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH₂Cl₂ (30 ml) was added dropwise to a magnetically stirred solution of [1S-[1β,2α(5Z),3α,4β]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/H₂O and stirred for 30 minutes. The products were extracted with EtOAc (80 ml×3). The combined EtOAc layers were washed with 3N-HCl (40 ml×3), saturated NaHCO₃, brine and dried over MgSO₄. Filtration and evaporation of solvent gave a white solid, which was crystallized from isopropyl ether to give the corresponding title tosylate in the form of needle crystals (4.23 g, 89%), m.p. 68°–70° C.

C. [1S-[1β,2α(5Z),3α,4β]]-7-[3-(Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°-100° C. for 2½ hours. After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO₄), filtered and freed of solvent in vacuo. The remaining solid (7.88 g) was recrystallized from isopropyl ether (~150 ml) to give corresponding phthalimide (6.35 g, 83%) TLC. Et₂O-hexane 2:1, UV+vanillin $R_f$=0.38.

The above phthalimide (5.05 g, 13.8 mmol) was dissolved in distilled CH₂Cl₂ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more CH₂Cl₂. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid K₂CO₃. The amine was extracted into CHCl₃ (3×100 ml), dried (MgSO₄) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D.
[1S-[1β,2α(5Z),3α,4β]]-7-[3-[[[[(1-Thioxohexyl)amino]acetyl]amino]methyl]-7-oxabicyclo[2.2.1]hept-2-yl]-5-heptanoic acid, methyl ester Part A acid compound (189 mg, 1 mmol) was dissolved in distilled THF (8 ml) in an argon atmosphere and cooled in an ice bath. Carbonyldiimidazole (CDI, 162 mg, 1 mmol) was added and the mixture was stirred cold for 1 hour and then for 1 hour at room temperature. After cooling in an ice bath, a solution of chiral amine prepared in Example 1 part C (267 mg, 1 mmol) in THF (3 ml) was added. The ice bath was removed and the mixture was stirred overnight at room temperature. The solvent was removed in vacuo. CHCl₃ (35 ml) was added to the residue. The solution was washed with 1N HCl (15 ml), 1N NaOH solution (15 ml) and H₂O (15 ml), dried (MgSO₄) and freed of solvent in vacuo leaving an oil (424 mg). This was chromatographed on silica gel (30 g, Baker for flash chromatography), eluting with ethyl acetate and 2% MeOH in ether to give the title compound a pale yellow oil (327.5 mg, 75%). TLC: silica gel, ethyl acetate, UV+vanillin; $R_f$=0.58.

EXAMPLE 2

[1S-[1β,2α(5Z),3α,4β]]-7-[3-[[[[(1-Thioxohexyl)amino]acetyl]amino]methyl]-7-oxabicyclo[2.2.1]hept-2-yl]-5-heptenoic acid The Example 1 methyl ester (325 mg, 0.74 mmol) was dissolved in distilled THF (25 ml) and water (5 ml) in an argon atmosphere. 1N LiOH solution was added and the mixture was stirred at room temperature 4 hours. After neutralizing with 1N HCl solution (5.6 ml) and addition of solid KCl, the layers were separated. The aqueous layer was extracted with CHCl₃ (3×25 ml). The combined organic layers (THF+CHCl₃) were washed with saturated NaCl solution (15 ml), dried (MgSO₄) and freed of solvent in vacuo leaving an oil (242 mg). This was chromatographed on silica gel (25 g, Baker for flash chromatography) eluting with 2% MeOH in ethyl acetate to give partially crystalline material (119 mg). This was triturated with Et₂O to give 65 mg of pale yellow solid. This was recrystallized from ethyl acetate (2–3 ml) to give title acid (54.9 mg, 17%), m.p. 123°–126° C.

TLC: silica gel, 5% MeOH in EtOAc, UV+vanillin, $R_f$=0.34 $[\alpha]_D$=−5.8° (c=0.67, MeOH).

Anal Calcd for C₂₂H₃₆O₄N₂S: C, 62.23; H, 8.55; N, 6.60; S, 7.55. Found: C, 61.99; H, 8.60; N, 6.51; S, 7.40.

EXAMPLE 3

[1S-[1β,2α(5Z),3α,4β]]-7-[3-[[[[(Butylamino)thioxo]amino]acetyl]amino]methyl]-7-oxabicyclo[2.2.1]hept-2-yl]-5-heptanoic acid, methyl ester A. N-[(Butylamino)thioxo]glycine, ethyl ester Butyl isothiocyanate (11.5 g, 10 mmol) is added dropwise to glycine ethyl ester hydrochloride (13.95 g, 10 mmol) and Et₃N (11.1 g, 11 mmol) in EtOH (20 ml) at 0° C. After the addition is completed, the reaction is allowed to warm to room temperature. Stirring is continued overnight at room temperature. The solvent is removed in vacuo and the residue is partitioned between CHCl₃ (100 ml) and H₂O (20 ml). The CHCl₃ layer is dried (MgSO₄) and evaporated off to give the title compound.

B. N-[(Butylamino)thioxo]glycine

Part A ester (10.9 g, 5 mmol) is suspended in NaOH (2N, 10 ml) at room temperature. The reaction is stirred for 5 hours. The reaction is washed with Et₂O (10 ml×2). The water layer is acidified with concentrated HCl to pH 1. The product is extracted with EtOAc (20 ml×3) and combined organic layers are washed with brine, and dried over MgSO₄. Filtration and evaporation of the solvent gives the title compound.

C.
[1S-[1β,2α(5Z),3α,4β]]-7-[3-[[[[(Butylamino)thioxo]amino]acetyl]amino]methyl]-7-oxabicyclo[2.2.1]hept-2-yl]-5-heptanoic acid, methyl ester Part B compound (190 mg, 1 mmol) is partially dissolved in distilled THF (8 ml) in an argon atmosphere. After cooling in an ice bath, carbonyl diimidazole (CDI) (162 mg, 1 mmol) is added. The mixture is stirred cold 1 hour and at room temperature 1½ hours. The solution is cooled in an ice bath and a solution of chiral amine prepared in Example 1 Part C (267 mg, 1 mmol) in THF (3 ml) is added. The cooling bath is removed and the mixture is left stirring overnight at room tem-

EXAMPLE 4

[1S-[1β,2α(5Z),3α,4β]]-7-[3-[[[[(Butylamino)thioxo]amino]acetyl]amino]methyl]-7-oxabicyclo[2.2.1]hept-2-yl]-5-heptenoic acid Example 3 methyl ester (212.5 mg, 0.50 mmol) is dissolved in distilled THF (20 ml) and water (4.8 ml) in an argon atmosphere. 1N LiOH solution (4.9 ml) is added and the mixture is stirred at room temperature 5 hours. The mixture is neutralized with 1N HCl solution (4.9 ml) and solid KCl is added. The layers are separated. The aqueous layer is reextracted with CHCl$_3$ (3×25 ml). The combined organic layers (THF and CHCl$_3$) are washed with saturated NaCl solution (15 ml), dried (MgSO$_4$) and freed of solvent in vacuo leaving an oil. This is chromatographed on silica gel to give the title compound.

EXAMPLE 5

[1S-[1β,2α(5Z),3α,4β]]-7-[3-[[[[Methyl(1-thioxohexyl)amino]acetyl]amino]methyl]-7-oxabicyclo[2.2.1]hept-2-yl]-5-heptenoic acid, methyl ester

A. [Methyl(1-thioxohexyl)amino]acetic acid

Following the procedure of Example 1 A (1), (2) and (3) except substituting sarcosine methyl ester hydrochloride of glycine ethyl ester hydrochloride, the title compound is obtained.

B. [1S-[1β,2α(5Z),3α,4β]]-7-[3-[[[[Methyl(1-thioxohexyl)amino]acetyl]amino]methyl]-7-oxabicyclo[2.2.1]hept-2-yl]-5-heptenoic acid, methyl ester Part A compound (203 mg, 1 mmol) is dissolved in distilled THF (8 ml) in an argon atmosphere and cooled in an ice bath. Carbonyldiimidazole (CDI) (162 mg, 1 mmol) is added and the mixture is stirred cold for 1 hour and then for 1 hour at room temperature. After cooling in an ice bath, a solution of chiral amine prepared in Example 1 part C (267 mg, 1 mmol) in THF (3 ml) is added. The ice bath is removed and the mixture is stirred overnight at room temperature. The solvent is removed in vacuo. CHCl$_3$ (35 ml) is added to the residue. The solution is washed with 1N HCl (15 ml), 1N NaOH solution (15 ml) and H$_2$O (15 ml), dried (MgSO$_4$) and freed of solvent in vacuo leaving an oil. This is chromatographed on silica gel to give the title compound.

EXAMPLE 6

[1S-[1β,2α(5Z),3α,4β]]-7-[3-[[[[Methyl(1-thioxohexyl)amino]acetyl]amino]methyl]-7-oxabicyclo[2.2.1]hept-2-yl]-5-heptenoic acid The Example 5 methyl ester (256 mg, 0.568 mmol) is dissolved in distilled THF (25 ml) and water (5 ml) in an argon atmosphere. 1N LiOH solution (5.6 ml) is added and the mixture was stirred at room temperature 4 hours. After neutralizing with 1N HCl solution (5.6 ml) and addition of solid KCl, the layers are separated. The aqueous layer is extracted with CHCl$_3$ (3×25 ml). The combined organic layers (THF+CHCl$_3$) are washed with saturated NaCl solution (15 ml), dried (MgaSO$_4$) and freed of solvent in vacuo leaving an oil. This was chromatographed on silica gel to give the title compound.

EXAMPLE 7

1[S-[1β,2α(5Z),3α,4β]]-7-[3-[[[[(Butoxythioxo)amino]acetyl]amino]methyl]-7-oxabicyclo[2.2.1]hept-2-yl]-5-heptenoic acid, methyl ester

A. N-(Butoxythioxo)glycine

Butyl chlorothioformate (15.25 g, 10 mmol) in Et$_2$O (10 ml) is added dropwise to glycine (7.5 g, 10 mmol) in Et$_2$O (10 ml) and NaOH solution (NaOH: 960 mg, H$_2$O: 10 ml). The reaction is vigorously stirred overnight at room temperature. The layers are separated and the water layer is washed with Et$_2$O (20 ml). The water layer is acidified with concentrated HCl. The product is extracted with EtOAc (40 ml×3). The combined EtOAc layers are washed with brine (20 ml×3) and dried over MgSO$_4$. Filtration and evaporation of solvent give the title compound.

B. [1S-[1β,2α(5Z),3α,4β]]-7-[3-[[[[(Butoxythioxo)amino]acetyl]amino]methyl]-7-oxabicyclo[2.2.1]hept-2-yl]-5-heptenoic acid, methyl ester The acid prepared in part A (191 mg, 1 mmol) is dissolved in distilled THF (8 ml) in an argon atmosphere. After cooling in an ice bath carbonyldiimidazole (CDI) (162 mg, 1 mmol) is added. The mixture is stirred cold 1 hour and at room temperature 1 hour. The mixture is again cooled in an ice bath and a solution of chiral amine (prepared in Example I part C, 267 mg, 1 mmol) in THF (3 ml) is added. The cooling bath is removed and the mixture is left stirring overnight at room temperature. The solvent is removed in vacuo. CHCl$_3$ (35 ml) is added. The solution is washed with 1N HCl (15 ml), 1N NaOH (15 ml) and H$_2$O (15 ml), dried (MgSO$_4$) and freed of solvent in vacuo. The remaining oil (433 mg) is chromatographed on silica gel to give the title compound.

EXAMPLE 8

[1S-[1β,2α(5Z),3α,4β]]-7-[3-[[[[(Butoxythioxo)amino]acetyl]amino]methyl]-7-oxabicyclo[2.2.1]hept-2-yl]-5-heptenoic acid The methyl ester prepared in Example 7 (174.2 mg, 0.396 mmol) is dissolved in distilled THF (16 ml) and water (3.8 ml) in an argon atmosphere and 1N LiOH solution (3.9 ml) is added. The mixture is stirred at room temperature 5½ hours, then neutralized with 1N HCl solution (3.8 ml). After adding solid KCl the layers are separated. The aqueous layer is extracted with CHCl$_3$ (3×25 ml). The combined organic layers (THF+CHCl$_3$) are washed with saturated NaCl solution (15 ml), dried (MgSO$_4$) and freed of solvent in vacuo having an oil (150 mg). This is chromatographed on silica gel to give the title compound.

EXAMPLE 9

[1S-[1β,2α(5Z),3α,4β]]-N-Methyl-7-[3-[[[[(1-Thioxohexyl)amino]acetyl]amino]methyl]-7-oxabicyclo[2.2.1]hept-2-yl]-5-heptenamide 40% MeNH$_2$ in H$_2$O (2 ml) is added to a magnetically stirred solution of ester prepared in Example 1 (153 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 10

[1S-[1β,2α(5Z),3α(R),4β]]-7-[3-[[[1-Oxo-2-[(1-thiox-ohexyl)amino]propyl]amino]methyl]-7-oxabicyclo[2.2.1]hept-2-yl]-5-heptenoic acid, methyl ester A. (2R)-2-[(1-Thioxohexyl)amino]propionic acid Following the procedure of Example 1A except substituting D-alanine ethyl ester hydrochloride for glycine ethyl ester hydrochloride, the title compound is obtained.

B.

[1S-[1β,2α(5Z),3α(R),4β]]-7-[3-[[[1-Oxo-2-[(1thiox-ohexyl)amino]propyl]amino]methyl]-7-oxabicyclo[2.2.1]hept-2-yl]-5-heptenoic acid, methyl ester Part A acid compound (1 mmol) and chiral amine prepared as described in Example 1 Part C (1 mmol) are coupled using CDI (1 mmol) as described in Example 5 Part B. The crude product is chromatographed on silica gel to give the title methyl ester.

EXAMPLE 11

[1S-[1β,2α(5Z),3α(R),4β]]-7-[3-[[[1-Oxo-2-[(1-Thiox-ohexyl)amino]propyl]amino]methyl]-7-oxabicyclo[2.2.1]hept-2-yl]-5-heptenoic acid The Example 10 methyl ester (215 mg, 0.49 mmol) is hydrolyzed with LiOH solution in a THF-water mixture as described in Example 6 to give title acid.

EXAMPLE 12

[1S-[1β,2α(5Z),3α,4β]]-7-[3-[[[2-Methyl-2-[(1thiox-ohexyl)amino]-1-oxopropyl]amino]methyl]-7-oxabicyclo[2.2.1]hept-2-yl]-5-heptenoic acid, methyl ester A. 2-Methyl-2-[(1-thioxohexyl)amino]propionic acid Following the procedure of Example 1A except substituting methyl 2-amino-2-methylpropionate hydrochloride for glycine ethyl ester hydrochloride, the title compound is obtained.

B.

[1S-[1β,2α(5Z),3α,4β]]-7-[3-[[[2-Methyl-2-[(1-thiox-ohexyl)amino]-1-oxopropyl]amino]methyl]-7-oxabicyclo[2.2.1]hept-2-yl]-5-heptenoic acid, methyl ester Part A compound (1 mmol) is reacted with CDI (1 mmol) and then with chiral amine prepared as described in Example 1 Part C (1 mmol) employing the method described in Example 1 Part D. The crude product is chromatographed on silica gel to give title ester.

EXAMPLE 13

[1S-[1β,2α(5Z),3α,4β]]-7-[3-[[[2-Methyl-2-[(1-Thiox-ohexyl)amino]-1-oxopropyl]amino]methyl]-7-oxabicyclo[2.2.1]hept-2-yl]-5-heptenoic acid The Example 12 methyl ester (0.51 mmol) is hydrolyzed with LiOH in a water-THF mixture as described in Example 6 to give title acid.

EXAMPLE 14

[1S-[1β,2α(5Z),3α,4β]]-7-[[[[(1-Thioxoheptyl)amino]acetyl]amino]methyl]-7-oxabicyclo[2.2.1]hept-2-yl]-5-heptenoic acid, methyl ester A. [(1-Thioxoheptyl)amino]acetic acid Following the procedure of Example 1A except substituting heptanoyl chloride for hexanoyl chloride, the title compound is obtained.

B.

[1S-[1β,2α(5Z),3α,4β]]-7-[3-[[[[(1-Thioxoheptyl)amino]acetyl]amino]methyl]-7-oxabicyclo[2.2.1]hept-2-yl]-5-heptenoic acid, methyl ester Part A compound (1 mmol) is reacted with CDI (1 mmol) and then with chiral amine (1 mmole) prepared as described in Example 1 Part C employing the method described in Example 5 Part B. The crude product is chromatographed on silica gel to give title ester.

EXAMPLE 15

[1S-[1β,2α(5Z),3α,4β]]-7-[3-[[[[(1-Thioxoheptyl)amino]acetyl]amino]methyl]-7-oxabicyclo[2.2.1]hept-2-yl]-5-heptenoic acid The Example 14 methyl ester (266.5 mg, 0.607 mmol) is hydrolyzed with LiOH in a water-THF mixture as described in Example 6 to give title acid.

EXAMPLE 16

[1S-(1β,2α,3α,4β)]-7-[3-[[[[(1-Thioxohexyl)amino]acetyl]amino]methyl]-7-oxabicyclo[2.2.1]hept-2-yl]heptanoic acid

A.

[1S-(1β,2α,3α,4β)]-7-[3-(Hydroxymethyl)-7-oxabicyclo[2.2.1]hept-2-yl]-heptanoic acid, methyl ester To 800 mg (3.0 mmole) of the [1S-[1β,2α(Z),-3α,4β]]-7-[3-(hydroxymethyl)-7-oxabicyclo[2.2.1]-hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

[1S-(1β,2α,3α,4β)]-7-[3-[[[[(1-Thioxohexyl)amino]acetyl]amino]methyl]-7-oxabicyclo[2.2.1]hept-2-yl]heptanoic acid Following the procedure of Examples 1 and 2 except substituting the Part A alcohol-ester for the alcohol ester employing in Example 1 Part B, the title product is obtained.

EXAMPLE 17

[1S-[1β,2α(5Z),3α,4β]]-7-[3-[[[(1-Oxo-[(1-thioxopentyl)amino]ethyl]amino]methyl]-7-oxabicyclo-[2.2.1]hept-2-yl]-5-heptenoic acid, methyl ester A. [(1-Thioxopentyl)amino]acetic acid Following the procedure of Example 1A except substituting pentanoyl chloride for hexanoyl chloride, the title compound is obtained.

B.
[1S-[1β,2α(5Z),3α,4β]]-7-[3-[[[(1-Oxo[(1-thioxopentyl-)amino]ethyl]amino]methyl]-7-oxabicyclo[2.2.1]hept-2-yl]-5-heptenoic acid, methyl ester Part A acid (1 mmol) is reacted with carbonyl diimidazole (1 mmol) followed by [1S-[1β,2α(5Z)-,3α,4β]]-7-[3-(aminomethyl)-7-oxabicyclo[2.2.1]hept-2-yl]-5-heptenoic acid, methyl ester (prepared as described in Example 1 Part C (1 mmole)). The crude product is chromatographed on silica gel (25 g, Baker for flash chromatography) eluting with 5-10% MeOH in Et₂O to give title product.

EXAMPLE 18

[1S-[1β,2α(5Z),3α,4β]]-7-[3-[[[1-Oxo[(1-thioxopentyl-)amino]ethyl]amino]methyl]-7-oxabicyclo[2.2.1]hept-2-yl]-5-heptenoic acid The Example 17 methyl ester (301 mg, 0.71 mmol) is hydrolyzed with LiOH in a THF-H₂O mixture as described in Example 6 to give title acid.

EXAMPLE 19

[1S-[1β, 2α(5Z),3α,4β]]-7-[3-[[[[(4-Thioxobiphenyl-)amino]acetyl]amino]methyl]-7-oxabicyclo[2.2.1]hept-2-yl]-5-heptenoic acid, methyl ester A. [(4-Thioxobiphenyl)amino]acetic acid Following the procedure of Example 1A except substituting 4-biphenylcarbonyl chloride for hexanoyl chloride, the title compound is obtained.

B.
[1S-[1β,2α(5Z),3α,4β]]-7-[3-[[[[(4-Thioxobiphenyl-)amino]acetyl]amino]methyl]-7-oxabicyclo[2.2.1]hept-2-yl]-5-heptenoic acid, methyl ester Part A acid (1 mmol) is reacted with carbonyl-diimidazole (1mmole) followed by [1S-[1β,2α(5Z)-,3α,4β]]-7-[3-(aminomethyl)-7-oxabicyclo[2.2.1]hept-2-yl]-5-heptenoic acid, methyl ester (1 mmole) as in Example 1, Part D. Stirring is continued overnight at room temperature. After the usual work up, the product is chromatographed on silica gel (30 g of Baker for flash chromatography), to give title ester.

EXAMPLE 20

[1S-[1β,2α(5Z),3α,4β]]-7-[3-[[[[(4-Thioxobiphenyl-)amino]acetyl]amino]methyl]-7-oxabicyclo[2.2.1]hept-2-yl]-5-heptenoic acid The Example 19 methyl ester (141 mg, 0.279 mmol), is hydrolyzed with LiOH as described in Example 6 to give title acid.

EXAMPLE 21

[1S-(1β,2α,3α,4β)]-7-[3-[[[[2-Methyl-2[(1-thioxohexyl-)amino]-1-oxopropyl]amino]methyl]-7-oxabicyclo[2.2.1]hept-2-yl]heptanoic acid Following the procedure of Example 16 except substituting the Example 12 Part A acid for the Example 1 Part A acid, the title acid is obtained.

EXAMPLE 22

[1S-[1β,2α(5Z),3α,4β]]-7-[3-[[[[(1-Thioxopropyl-)amino]acetyl]amino]methyl]-7-oxabicyclo[2.2.1]hept-2yl]-5-heptenoic acid Following the procedure of Examples 1 and 2 except substituting propanoyl chloride for hexanoyl chloride, the title compound is obtained.

EXAMPLE 23

[1S-[1β,2α(5Z),3α,4β]]-7-[3-[[[[(1-Thioxoethyl-)amino]acetyl]amino]methyl]-7-oxabicyclo[2.2.1]hept-2-yl]-5-heptenoic acid Following the procedure of Examples 1 and 2 except substituting acetyl chloride for 6-hexanoyl chloride, the title compound is obtained.

EXAMPLE 24

[1S-[1β,2α(5Z),3α,4β]]-7-[3-[[[[(1-Thioxo-2-butenyl-)amino]acetyl]amino]methyl]-7-oxabicyclo[2.2.1]hept-2-yl]-5-heptenoic acid Following the procedure of Examples 1 and 2 except substituting 2-butenoyl chloride for hexanoyl chloride, the title compound is obtained.

EXAMPLE 25

[1S-[1β,2α(5Z),3α,4β]]-7-[3-[[[[(1-Thioxo-4-pentynyl-)amino]acetyl]amino]methyl]-7-oxabicyclo[2.2.1]hept-2-yl]-5-heptenoic acid Following the procedure of Examples 1 and 2 except substituting 4-pentynoyl chloride for hexanoyl chloride, the title compound is obtained.

EXAMPLE 26

[1S-[1β,2α(5Z),3α,4β]]-7[3-[[[[(Pentylamino)thiocarbonyl]amino]acetyl]amino]methyl]-7-oxabicyclo[2.2.1-]hept-2-yl]-5-heptenoic acid Following the procedure of Examples 3 and 4 except substituting n-pentyl isocyanate for n-butyl isocyanate, the title compound is obtained.

EXAMPLE 27

[1S-[1β,2α(5Z),3α,4β]]-7-[3-[[[[(Phenylamino)thiocarbonyl]amino]acetyl]amino]methyl]-7-oxabicyclo[2.2.1-]hept-2-yl]-5-heptenoic acid Following the procedure of Examples 3 and 4 except substituting phenyl isocyanate for n-butyl isocyanate, the title compound is obtained.

EXAMPLE 28

[1S-[1β,2α(5Z),3α,4β]]-7-[3-[[[[(Phenylthiocarbonyl-)amino]acetyl]amino]methyl]-7-oxabicyclo[2.2.1]hept-2-yl]-5-heptenoic acid Following the procedure of Examples 1 and 2 except substituting benzoyl chloride for hexanoyl chloride, the title compound is obtained.

EXAMPLE 29

[1S-[1β,2α(5Z),3α,4β]]-7-[3-[[[1-Oxo-3-[ethyl(phenylthiocarbonyl)amino]propyl]amino]methyl]-7-oxabicyclo[2.2.1]hept-2-yl]-5-heptenoic acid Following the procedure of Examples 5 and 6 except substituting 3-(ethylamino)propionic acid ethyl ester hydrochloride for sarcosine methyl ester hydrochloride and benzoyl chloride for hexanoyl chloride, the title compound is obtained.

EXAMPLE 30

[1S-[1β,2α(5Z),3α,4β]]-7-[3-[[[[(Benzyloxythiocarbonyl)amino]acetyl]amino]methyl]-7-oxabicyclo[2.2.1]hept-2-yl]-5-heptenoic acid Following the procedure of Examples 7 and 8 except substituting benzyl chloroformate for n-butyl chloroformate, the title compound is obtained.

EXAMPLE 31

[1S-(1β,2α,3α,4β)]-7-[3-[[[[(1-Thioxobutyl)amino]acetyl]amino]methyl]-7-oxabicyclo[2.2.1]hept-2-yl]heptanoic acid Following the procedure of Example 16 except substituting butanoyl chloride for hexanoyl chloride, the title compound is obtained.

EXAMPLE 32

[1S-(1β,2α,3α,4β)]-7-[3-[[[[(1-Thioxo-2-propenyl)amino]acetyl]amino]methyl]-7-oxabicyclo[2.2.1]hept-2-yl]heptanoic acid Following the procedure of Example 16 except substituting 2-propenyl chloride for hexanoyl chloride, the title compound is obtained.

EXAMPLE 33

[1S-(1β,2α,3α,4β)]-7-[3-[[[[(1-Thioxo-4-pentynyl)amino]acetyl]amino]methyl]-7-oxabicyclo[2.2.1]hept-2-yl]heptanoic acid Following the procedure of Example 16 except substituting 4-pentynoyl chloride for hexanoyl chloride, the title compound is obtained.

EXAMPLE 34

[1S-(1β,2α,3α,4β)]-7-[3-[[[[[(Phenylamino)thiocarbonyl]amino]acetyl]amino]methyl]-7-oxabicyclo[2.2.1]hept-2-yl]heptanoic acid Following the procedure of Examples 16 and 3 except substituting phenyl isocyanate for n-butyl isocyanate in Example 3 Part A, the title compound is obtained.

EXAMPLE 35

[1S-(1β,2α,3α,4β)]-7-[3-[[[1-Oxo-4-[propyl(1-thioxobenzyl)amino]butyl]amino]methyl]-7-oxabicyclo[2.2.1]hept-2-yl]heptanoic acid Following the procedure of Examples 16 and 5 except substituting 4-(propylamino)butanoic acid ethyl ester hydrochloride for sarcosine methyl ester hydrochloride in Example 5 Part A, the title compound is obtained.

EXAMPLE 36

[1S-(1β,2α,3α,4β)]-7-[3-[[[[(Benzyloxythiocarbonyl)amino]acetyl]amino]methyl]-7-oxabicyclo[2.2.1]hept-2-yl]heptanoic acid Following the procedure of Examples 7 and 16 except substituting benzyl chloroformate for n-butyl chloroformate, the title compound is obtained.

EXAMPLE 37

[1S-[1β,2α(5Z),3α,4β]]-7-[3-[2-[[[(1-Thioxohexyl)amino]acetyl]amino]ethyl]-7-oxabicyclo[2.2.1]hept-2-yl]-5-heptenoic acid

A.

[1S-[1β,2α(Z),3α,4β]]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P$^+$—CH$_2$OCH$_3$Cl$^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl, and extracted with ether (4×200 ml). The combined ether phases were washed with NaCl, saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1]hept-2-yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1S-[1β,2α(5Z),3α,4β]]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[1S-[1β,2α(Z),3α,4β]]-7-[3-[2-[[[(1-Thioxohexyl)amino]acetyl]amino]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 38

[1S-(1β,2α,3α,4β)]-7-[3-[2-[[[(1-Thioxohexyl)amino]acetyl]amino]ethyl]-7-oxabicyclo[2.2.1]hept-2-yl]heptanoic acid Following the procedure of Examples 37 and 1 except substituting [1S-(1β,2α,3α,4β)]-7-[3-formyl-7-oxabicyclo[2.2.1]hept-2-yl]heptanoic acid, methyl ester for [1S-[1β,2α(Z),3α,4β]]-7-[3-formyl-7-oxabicyclo[2.2.1]hept-2-yl]-5-heptenoic acid, methyl ester, the title compound is obtained.

EXAMPLE 39

[1S-[1β,2α(5Z),3α,4β]-7-[3-[2-[[[(1-Thioxopropyl)amino]acetyl]amino]ethyl]-7-oxabicyclo[2.2.1]hept-2-yl]-5-heptenoic acid Following the procedure of Example 37 except substituting propionyl chloride for hexanoyl chloride, the title compound is obtained.

EXAMPLE 40

[1S-(1β,2α,3α,4β)]-7-[3-[2-[[[(1-Thioxo-2-butenyl)amino]acetyl]amino]ethyl]-7-oxabicyclo[2.2.1]hept-2-yl]heptanoic acid Following the procedure of Examples 37 and 16 except substituting 2-butenoyl chloride for hexanoyl chloride, the title compound is obtained.

EXAMPLE 41

[1S-[1β,2α(5Z),3α,4β]]-7-[3-[2-[[[[(Phenylamino)thiocarbonyl]amino]acetyl]amino]ethyl]-7-oxabicyclo[2.2.1]hept-2-yl]-5-heptenoic acid Following the procedure of Examples 37 and 3 except substituting phenyl isocyanate for n-butyl isocyanate, the title compound is obtained.

EXAMPLE 42

[1S-[1β,2α(5Z),3α,4β]]-7-[3-[2-[[1-Thioxo-3-[ethyl(1-oxophenylmethyl)amino]propyl]amino]ethyl]-7-oxabicyclo[2.2.1]hept-2-yl]-5-heptenoic acid Following the procedure of Examples 37 and 5 except substituting 3-(ethylamino)propionic acid ethyl ester hydrochloride for sarcosine methyl ester hydrochloride and benzoyl chloride for hexanoyl chloride, the title compound is obtained.

EXAMPLE 43

[1S-[1β,2α(5Z),3α,4β]]-7-[3-[4-[[[(1-Thioxohexyl)amino]acetyl]amino]butyl]-7-oxabicyclo[2.2.1]hept-2-yl]-5-heptenoic acid

A.

[1S-[1β,2α(5Z),3α,4β]]-7-[3-(3-Oxo)propyl-7-oxabicyclo[2.2.1]hept-2-yl]-5-heptenoic acid, methyl ester Following the procedure of Example 37 Part A except substituting [1S-[1β,2α(Z),3α,4β]]-7-[3-(2-oxo)ethyl-7oxabicyclo[2.2.1]hept-2-yl]-5-heptenoic acid, methyl ester for [1S-[1β,2α(Z),3α,4β]]-7-[3-formyl-7-oxabicyclo[2.2.1]hept-2-yl]-5-heptenoic acid, methyl ester, the title A compound is obtained.

B.

[1S-[1β,2α(Z),3α,4β]]-7-[3-(4-Oxo)butyl-7-oxabicyclo[2.2.1]hept-2-yl]-5-heptenoic acid, methyl ester Following the procedure of Example 37 Part A except substituting the aldehyde from Part A above for [1S-[1β,2α(Z),3α,4β]]-7-[3-formyl-7-oxabicyclo[2.2.1]hept-2-yl]-5-heptenoic acid, methyl ester, the title B compound is obtained.

C.

[1S-[1β,2α(Z),3α,4β]]-7-[3-(4-Hydroxybutyl)-7-oxabicyclo[2.2.1]hept-2-yl]-5-heptenoic acid, methyl ester Following the procedure of Example 37 Part B except substituting the title B aldehyde for [1S-[1β,2α(Z),3α,4β]]-7-[3-(2-oxo)ethyl-7-oxabicyclo[2.2.1]hept-2-yl]-5-heptenoic acid, methyl ester, the title C alcohol is obtained.

D.

[1S-[1β,2α(Z),3α,4β]]-7-[3-[4-[[[(1-Thioxohexyl)amino]acetyl]amino]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 44

[1S-[1β,2α(5Z),3α,4β]]-8-[3-[[[[(1-Thioxohexyl)amino]acetyl]amino]methyl]-7-oxabicyclo[2.2.1]hept-2-yl]-5-octenoic acid

A.

[1S-(1β,2α,3α,4β)]-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XIII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO$_4$ and concentrated in vacuo. The solid residue was triturated with hexane (1 liter), filtered, and dried in vacuo to yield 220 g (100%) of desired compound (hemiacetal F in reaction sequence C), m.p. 104°-105° C., [α]$_D$=+27° c=1 MeOH.

TLC: Silica gel; EtOAc; R$_f$=0.3; Ce(SO$_4$)$_2$.

The above Wittig procedure was repeated on the hemiacetal F used in place of hemiacetal XIII to form the title aldehyde.

B.
[1S-[1β,2α(Z),3α,4β]]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane (CH$_2$N$_2$) in Et$_2$O to give the title compound.

C.
[1S-[1β,2α(Z),3α,4β]]-8-[3-[[[(1-Thioxohexyl)amino]acetyl]amino]methyl]-7-oxabicyclo[2.2.1]hept-2-yl]-5-octenoic acid Following the procedure of Examples 1 and 2 except substituting the title B ester for the ester used in Example 1 Part B, the title compound is obtained.

EXAMPLE 45
[1S-[1β,2α(Z),3α,4β]]-6-[3-[[[(1-Thioxohexyl)amino]acetyl]amino]methyl]-7-oxabicyclo[2.2.1]hept-2-yl]-1-(1H-tetrazol-5-yl)-4-hexene

A.
[1S-[1β,2α(Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene choride eluant to provide 2 g of title A compound.

B.
[1S-[1β,2α(5Z),3α,4β]]-6-[3-[[[(1-Thioxohexyl)amino]acetyl]amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part B, the title compound is obtained.

EXAMPLE 46
[1S-[1β,2α(5Z),3α,4β]]-7-[3-[[[[(1-Thioxohexyl)amino]acetyl]amino]methyl]-7-oxabicyclo[2.2.1]hept-2-yl]-N-hydroxy-N-methyl-5-heptenamide A solution of Example 2 acid (0.82 mmole) in dry THF (5.0 ml) is treated with carbonyldiimidazole (162 mg, 1 mmol) and stirred at 0° C. one hour and at room temperature one hour. Methylhydroxylamine hydrochloride (139.8 mg; 1.64 mmole; 2 eq.) and triethylamine (0.34 ml; 2.46 mmole; 3 eq.) in tetrahydrofuran (2 ml) are added at 0° C. The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 47
[1S-[1β,2α(6Z),3α,4β]]-7-[3-[[[[(1-Thioxohexyl)amino]acetyl]amino]methyl]-7-oxabicyclo[2.2.1]hept-2-yl]-6-heptenoic acid

A.
[1S-[1β,2α(6Z),3α,4β]]-7-[3-(Hydroxymethyl)-7-oxabicyclo[2.2.1]hept-2-yl]heptenoic acid, methyl ester Dried (5-carboxypentyl)triphenylphosphonium bromide (277.44 g, 60 mmol) was suspended in dry distilled THF (100 ml) in an argon atmosphere and cooled in an ice bath. While stirring, a solution of K-t-amylate (79.2 ml of 1.44M., 114 mmol) in toluene was added dropwise over 40 minutes. The ice bath was then removed and the orange mixture was stirred at temperature 6.5 hours. A solution of chiral hemiacetal XIII (3.12 g, 20 mmol, reaction sequence G, prepared as described in Example 3 of the U.S. Pat. No. 4,143,054) in distilled THF (30 ml) was added dropwise. The mixture was left stirring overnight at room temperature, then quenched by adding acetic acid dropwise. Most of the solvent was removed in vacuo and saturated NaCl solution (125 ml) was added. The product was extracted into EtOAc (4×100 ml). The combined EtOAc extracts were extracted with saturated NaHCO$_3$ solution (4×100 ml). The NaHCO$_3$ solution was acidified with HCl and then the product was extracted into CHCl₃ (4×100 ml). The chloroform extracts were dried (MgSO₄), filtered and freed of solvent in vacuo. The residue was partially dissolved in ether, cooled in an ice bath and treated with excess diazomethane solution. After stirring at room temperature 30 minutes, the excess diazomethane was destroyed by adding HOAc dropwise. The ether solution was washed with saturated NaHCO₃ solution, dried (MgSO₄), and freed of solvent in vacuo leaving an oil. Flash chromatography on silica gel, eluting with ether:-pet ether 4:3 and ether gave the title compound, 3.867 g (72%).

B.

[1S-[1β,2α(6Z),3α,4β]]-7-[3-[[[[(1-Thioxohexyl)amino]acetyl]amino]methyl]-7-oxabicyclo[2.2.1]hept-2-yl]-6-heptenoic acid Following the procedure of Examples 1 and 2 except substituting the Part A ester for the hydroxymethyl compound used in Example 1 Part B, the title compound is obtained.

EXAMPLE 48

[1S-[1β,2α(2E),3α,4β]]-7-[3-[[[[(1-Thioxohexyl)amino]acetyl]amino]methyl]-7-oxabicyclo[2.2.1]hept-2-yl]2-heptenoic acid

A.

[1S-(1β,2α,3α,4β)]-5-[3-(Hydroxymethyl)-7-oxabicyclo[2.2.1]hept-2-yl]pentanal

Following the procedure of Example 47 Part A, except substituting [1S-(1β,2α,3α,4β)]-3-[3-(hydroxymethyl)-7-oxabicyclo[2.2.1]hept-2-yl]propionaldehyde for the hemiacetal XIII (see reaction sequence G or H), [1S-(1β,2α,3α,4β)]-4-[3-(hydroxymethyl)-7-oxabicyclo[2.2.1]hept-2-yl]butanal is obtained. Then by repeating the procedure of Example 47 Part A on [1S-(1β,2α,3α,4β)]-4-[3-(hydroxymethyl)-7-oxabicyclo[2.2.1]hept-2-yl]butanal, the title A aldehyde is produced.

B.

[1S-[1β,2α(2E),3α,4β]]-7-[3-(Hydroxymethyl)-7-oxabicyclo[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) estes. Purification is affected by chromatography to afford the pure title ester.

C.

[1S-[1β,2α(2E),3α,4β]]-7-[3-[[[[(1-Thioxohexyl)amino]acetyl]amino]methyl]-7-oxabicyclo[2.2.1]hept-2-yl]-2-heptenoic acid Following the procedure of Example 1 except substituting the Part B ester for the ester used in Example 1 Part B, the title compound is obtained.

EXAMPLE 49

[1S-[1β,2α(5Z),3α,4β]]-7-[3-[(Methylamino)methyl]-7-oxabicyclo[2.2.1]hept-2-yl]-5-heptenoic acid, methyl ester Chiral amine from Example 1, Part C (1 mmole) and N,N-dimethylformamide dimethylacetal (1.5 mmole) are dissolved in CH₂Cl₂ (6 ml). The reaction is stirred at room temperature overnight. The solvent and the excess reagent are evaporated to give crude amidine, which is dissolved in CH₂Cl₂ (5 ml). Methyl triflate (2 mmole) is added into the reaction at room temperature and the reaction is stirred for 1 hour at room temperature. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated NaHCO₃. The water layer is extracted with ethyl ether, which is dried over MgSO₄. Filtration and evaporation of the solvent leave a crude product, which is purified by silica gel column to give the title compound.

The title compound is then employed in place of the chiral amine from Example 1 Part C to prepare compounds of the invention wherein R¹ is CH₃.

EXAMPLE 50

[1S-[1β,2α(5Z),3α,4β]]-7-[3-[[[[(1-Thioxononyl)amino]acetyl]amino]methyl]-7-oxabicyclo[2.2.1]hept-2-yl]-5-heptenoic acid, methyl ester A. [(1-Thioxononyl)amino]acetic acid Following the procedure of Example 1A except substituting nonanoyl chloride for hexanoyl chloride, the title compound is obtained.

B.

[1S-[1β,2α(5Z),3α,4β]]-7-[3-[[[[(1-Thioxononyl)amino]acetyl]amino]methyl]-7-oxabicyclo[2.2.1]hept-2-yl]-5-heptenoic acid, methyl ester Part A compound (1 mmol) is reacted with carbonyldiimidazole (1 mmol) followed by Examle 1 Part C chiral amine as described in Example 1 Part D. The crude product is chromatographed on silica gel to give the title ester.

EXAMPLE 51

[1S-[1β,2α(5Z),3α,4β]]-7-[3-[[[[(1-Thioxononyl)amino]acetyl]amino]methyl]-7-oxabicyclo[2.2.1]hept-2-yl]-5-heptenoic acid The Example 50 methyl ester (302 mg, 6.5 mmol) is hydrolyzed with LiOH in a THF-H₂O mixture as described in Example 2 to give title acid.

EXAMPLE 52

[1S-[1β,2α(5Z),3α,4β]]-7-[3-[[[[(1-Thioxooctyl)amino]acetyl]amino]methyl]-7-oxabicyclo[2.2.1]hept-2-yl]-5-heptenoic acid, methyl ester A. [(1-Thioxooctyl)amino]acetic acid Following the procedure of Example 1A except substituting octanoyl chloride for hexanoyl chloride, the title compound is obtained.

B.

[1S-[1β,2α(5Z),3α,4β]]-7-[3-[[[[(1-Thioxooctyl-)amino]acetyl]amino]methyl]-7-oxabicyclo[2.2.1]hept-2-yl]-5-heptenoic acid, methyl ester Part A compound (1 mmol) is reacted with carbonyldiimidazole (1 mmol), followed by Example 1 Part C chiral amine (1 mmol) as described in Example 1 Part D. The crude product is chromatographed on silica gel (30 g, Baker for flash chromatography) to give title ester.

EXAMPLE 53

[1S-[1β,2α(5Z),3α,4β]]-7-[3-[[[[(1-Thioxooctyl-)amino]acetyl]amino]methyl]-7-oxabicyclo[2.2.1]hept-2-yl]-5-heptenoic acid The Example 52 methyl ester (329 mg, 0.726 mmol) is hydrolyzed with LiOH in A THF-H$_2$O mixture as described in Example 2 to give title acid.

EXAMPLES 54 TO 81

Following the procedures outlined in the specification and described in the above working Examples, the following compounds may be prepared.

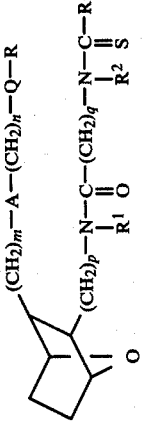

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 54. | 2 | CH=CH | $CH_2$ | CH=CH | $CO_2H$ | 1 | H | $(CH_2)_2$ | $CH_3$ | H |
| 55. | 3 | $(CH_2)_2$ | $(CH_2)_2$ | $CH_2$ | $CH_2OH$ | 2 | $C_2H_5$ | $(CH_2)_3$ | H | $CH_3$ |
| 56. | 4 | CH=CH | $(CH_2)_3$ | $\underset{-CH-}{\overset{OH}{\mid}}$ | $\underset{\underset{H}{N}}{\overset{N=N}{\diagdown}}\!\!\!\!\diagup$ | 3 | H | $(CH_2)_4$ | H | $-CH_2-CH=CH-CH_3$ |
| 57. | 1 | $(CH_2)_2$ | $(CH_2)_4$ | $\underset{-CH-}{\overset{F\phantom{x}F}{\diagdown\diagup}}$ | $\underset{CN(CH_3)C_2H_5}{\overset{O}{\parallel}}$ | 1 | $CH_3$ | $(CH_2)_5$ | $CH_3$ | $-C\equiv C-CH_3$ |
| 58. | 0 | CH=CH | $(CH_2)_5$ | $\underset{-C-}{\overset{F\phantom{x}F}{\diagdown\diagup}}$ | $\underset{\underset{CH_3}{CN-OH}}{\overset{O}{\parallel}}$ | 2 | H | $(CH_2)_6$ | $C_2H_5$ | $-CH_2-CH_2-C\equiv CH$ |
| 59. | 2 | CH=CH | $\underset{-CH-}{\overset{CH_3}{\mid}}$ | CH=CH | $\underset{\underset{H}{CN-OCH_3}}{\overset{O}{\parallel}}$ | 3 | $C_2H_5$ | $(CH_2)_7$ | $C_3H_7$ | $\underset{-CH_2-C=C-CH_3}{\overset{H\phantom{x}H}{\mid\phantom{x}\mid}}$ |
| 60. | 3 | $(CH_2)_2$ | $\underset{-C-}{\overset{\overset{CH_3}{\mid}}{\underset{CH_3}{\mid}}}$ | $CH_2$ | $\underset{\underset{CH_3}{CN-OC_2H_5}}{\overset{O}{\parallel}}$ | 4 | H | $\underset{-CH-}{\overset{CH_3}{\mid}}$ | $C_4H_9$ | $C_6H_5$ |
| 61. | 4 | $(CH_2)_2$ | $(CH_2)_4$ | $\underset{-CH-}{\overset{OH}{\mid}}$ | $\underset{CNHC_6H_5}{\overset{O}{\parallel}}$ | 1 | $C_3H_7$ | $-CH_2-$ | $C_5H_{11}$ | $C_6H_5$ |
| 62. | 1 | CH=CH | $\underset{-C-CH_2-}{\overset{\overset{CH_3}{\mid}}{\underset{CH_3}{\mid}}}$ | $\underset{-C-}{\overset{F\phantom{x}F}{\diagdown\diagup}}$ | $CO_2Li$ | 2 | H | $\underset{-CH_2-CH-}{\overset{CH_3}{\mid}}$ | H | $CH_2C_6H_5$ |
| 63. | 0 | CH=CH | $\underset{-CH-CH-}{\overset{\overset{CH_3\phantom{x}CH_3}{\mid\phantom{xx}\mid}}{}}$ | $\underset{-C-}{\overset{F\phantom{x}F}{\diagdown\diagup}}$ | $CO_2Na$ | 3 | $CH_3$ | $\underset{-CH_2-C-}{\overset{\overset{CH_3}{\mid}}{\underset{CH_3}{\mid}}}$ | H | $-(CH_2)_2C_6H_5$ |

-continued

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 64. | 1 | $(CH_2)_2$ | $-C(CH_3)F-CH_2-$ | CH=CH | $CO_2$glucamine salt | 4 | $C_2H_5$ | $-CH_2-CH(CH_3)-CH_2-$ | H | $-C_6H_4-p-CH_3$ |
| 65. | 2 | CH=CH | $-CH(F)-CH(F)-$ | $CH_2$ | $CO_2$tris salt | 1 | H | $-(CH_2)_3-$ | $CH_3$ | $-C_6H_4-p-OH$ |
| 66. | 3 | $(CH_2)_2$ | $-CF_2-CH_2-$ | $-CH(OH)-$ | $CH_2OH$ | 2 | $C_4H_9$ | $-CH_2-CH(C_2H_5)-$ | $CH_3$ | $-OCH_3$ |
| 67. | 4 | $(CH_2)_2$ | $-(CH_2)_5-$ | $-CF_2-$ | triazole (N—N / \\ CH_3—C / N—N H) | 3 | H | $-CH_2-C(CH_3)(H)-CH_2-$ | $CH_3$ | $-OC_2H_5$ |
| 68. | 0 | CH=CH | $-CH_2-CH(CH_3)-CH_2-$ | $-CF_2-$ | $-C(=O)NH_2$ | 4 | $CH_2$ | $-C(CH_3)_2-CH_2-$ | $C_2H_5$ | $-OCH_2C_6H_5$ |
| 69. | 0 | $(CH_2)_2$ | $-C(CH_3)_2-CH_2-$ | — | $-C(=O)N(OH)H$ | 1 | $C_2H_5$ | $(CH_2)_2$ | $CH_3$ | $-NH_2$ |
| 70. | 1 | CH=CH | $CH_2$ | — | $-C(=O)N(CH_3)_2$ | 2 | $H_5$ | $-CH_2-$ | H | $-NHCH_3$ |
| 71. | 2 | $(CH_2)_2$ | $(CH_2)_2$ | $CH_2$ | $-C(=O)N(CH_3)(OH)$ | 3 | $CH_3$ | $-CH_2-C(CH_3)_2-$ | $C_4H_9$ | $-NHC_6H_5$ |
| 72. | 3 | CH=CH | $(CH_2)_3$ | — | $CO_2H$ | 4 | $C_2H_5$ | $-CH_2-CH(CH_3)-CH(CH_3)-CH_2-$ | $CH_3$ | $NCH_3(C_2H_5)$ |

-continued $$-(CH_2)_m-A-(CH_2)_n-Q-R$$
$$(CH_2)_p-N-C-(CH_2)_q-N-C-R^3$$
$$\quad\quad\quad R^1\ O\quad\quad\quad R^2\ S$$

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 73. | 4 | $(CH_2)_2$ | $(CH_2)_4$ | CH=CH | $CH_2OH$ | 1 | $C_3H_7$ | $(CH_2)_2$ | $C_2H_5$ | $-N(CH_3)_2$ |
| 74. | 0 | CH=CH | $\begin{array}{c}F\\|\\CH_3C-\\|\\CH_2C-\\|\\F\end{array}$ | $\begin{array}{c}\phantom{.}\\-CH_2\end{array}$ | $\begin{array}{c}N-N\\\|\phantom{xx}\|\\\phantom{x}\diagdown\phantom{x}\diagup\\\phantom{xxx}C\\\phantom{xxx}\|\\\phantom{xxx}CH_3\\\text{N-H}\end{array}$ | 2 | $C_4H_9$ | $(CH_2)_3$ | $CH_3$ | H |
| 75. | 1 | $(CH_2)_2$ | $\begin{array}{c}CH_3\\|\\CH_3-C-\\|\\-CH_2-\end{array}$ | $\begin{array}{c}OH\\|\\-CH-\end{array}$ | $\begin{array}{c}O\\\|\|\\CN(C_2H_5)_2\end{array}$ | 3 | $C_5H_{11}$ | $\begin{array}{c}F\\|\\-CH-CH_2-\end{array}$ | $C_3H_7$ | $C_4H_9$ |
| 76. | 2 | CH=CH | $(CH_2)_5$ | $\begin{array}{c}F\\|\\-CH-\end{array}$ | $\begin{array}{c}O\\\|\|\\CNHC_6H_5\end{array}$ | 4 | H | $\begin{array}{c}F\ F\\\diagdown\diagup\\-C-CH_2\end{array}$ | $CH_4H_9$ | $-(CH_2)_2CH=CHCH_3$ |
| 77. | 3 | $(CH_2)_2$ | $\begin{array}{c}CH_3\ F\\|\ \ |\\-CH_2-CH-\end{array}$ | $\begin{array}{c}F\ F\\\diagdown\diagup\\-C-\end{array}$ | $CH_2OH$ | 1 | H | $(CH_2)_2$ | H | $C_6H_5$ |
| 78. | 4 | $(CH_2)_2$ | $(CH_2)_2$ | CH=CH | $\begin{array}{c}N-N\\\|\phantom{xx}\|\\\phantom{x}\diagdown\phantom{x}\diagup\\\phantom{xxx}C\\\phantom{xxx}\|\\\phantom{xxx}CH_3\\\text{N-H}\end{array}$ | 2 | H | $CH_2$ | H | $-CH_2C_6H_5$ |
| 79. | 0 | CH=CH | $(CH_2)_3$ | $\begin{array}{c}OH\\|\\-CH-\end{array}$ | $CO_2CH_3$ | 3 | $CH_3$ | $(CH_2)_3$ | $C_3H_7$ | $-OC_4H_9$ |
| 80. | 2 | $(CH_2)_2$ | $(CH_2)_4$ | $CH_2$ | $CO_2CH_3$ | 4 | $CH_3$ | $(CH_2)_8$ | H | $-O(CH_2)_2C_6H_5$ |
| 81. | 3 | CH=CH | $(CH_2)_5$ | — | $CO_2H$ | 1 | $CH_3$ | $(CH_2)_{10}$ | H | $-NCH_3(C_6H_5)$ |

What is claimed is:

1. A compound having the structure

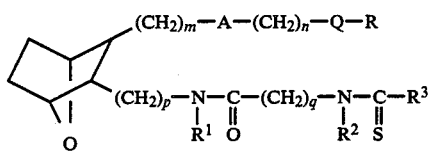

including all stereoisomers thereof, wherein m is 0 to 4; A is —CH=CH— or —CH₂—CH₂—; n is 1 to 5; Q is —CH=CH—, —CH₂—,

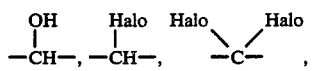

or a single bond; R is $CO_2H$, $CO_2$alkyl, $CO_2$ alkali metal, $CO_2$ polyhydroxyamine salt, —CH₂OH,

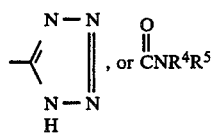

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl containing 2 to 12 carbons, lower alkynyl containing 2 to 12 carbons, aryl, arylalkyl, lower alkoxy, aralkyloxy, amino, alkylamino, or arylamino, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

aryl alone or as part of another group contains 6 to 10 carbons in the ring portion and is unsubstituted or is substituted with 1 or 2 lower alkyl groups, 1 or 2 halogens, 1 or 2 hydroxy groups, 1 or 2 lower alkoxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; and cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein $R^3$ is alkyl or alkoxy.

3. The compound as defined in claim 1 wherein A is CH=CH.

4. The compound as defined in claim 1 wherein m is 1 and n is 1 to 4.

5. The compound as defined in claim 1 wherein p is 1 and q is 1.

6. The compound as defined in claim 1 wherein Q is a single bond or $CH_2$.

7. The compound as defined in claim 1 wherein R is $CO_2$ alkyl or $CO_2H$.

8. The compound as defined in claim 1 wherein $R^1$ is H and $R^2$ is H or $CH_3$.

9. The compound as defined in claim 1 wherein m is 1, n is 2 to 4, Q is $CH_2$, a single bond, CH=CH,

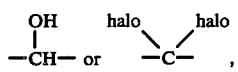

R is $CO_2$alkyl, $CO_2H$, $CH_2OH$, or

p is 1, $R^1$ is H, q is 1, $R^2$ is H or alkyl and $R^3$ is alkyl or alkoxy.

10. The compound as defined in claim 1 having the name [1S-[1β,2α(5Z),3α,4β]]-7-[3-[[[[(1-thioxohexyl)amino]acetyl]amino]methyl]-7-oxabicyclo[2.2.1]hept-2-yl]-5-heptenoic acid or esters thereof, including all stereoisomers thereof.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 0.1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

16. A method of treating peripheral vascular diseases, which comprises topically or systemically administering to a mammalian host an effective amount of a compound as defined in claim 1 or a pharmaceutically acceptable salt thereof.

* * * * *